(12) United States Patent
Liu et al.

(10) Patent No.: US 10,011,585 B2
(45) Date of Patent: Jul. 3, 2018

(54) FACTOR XIA INHIBITORS

(71) Applicant: Merck Sharp & Dohme Corp., Rahway, NJ (US)

(72) Inventors: Weiguo Liu, Princeton, NJ (US); Scott D Edmondson, Clark, NJ (US); Zhuyan Guo, Scotch Plains, NJ (US); Alan Hruza, Hackettstown, NJ (US); Sung-Sau So, Verona, NJ (US); Wanying Sun, Edison, NJ (US); Amjad Ali, Freehold, NJ (US); Rongze Kuang, Green Brook, NJ (US); Ying-Duo Gao, Holmdel, NJ (US); Anthony K Ogawa, New Providence, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/329,635

(22) PCT Filed: Jul. 23, 2015

(86) PCT No.: PCT/US2015/041646
§ 371 (c)(1),
(2) Date: Jan. 27, 2017

(87) PCT Pub. No.: WO2016/018701
PCT Pub. Date: Feb. 4, 2016

(65) Prior Publication Data
US 2017/0240523 A1    Aug. 24, 2017

Related U.S. Application Data

(60) Provisional application No. 62/029,772, filed on Jul. 28, 2014.

(51) Int. Cl.
*C07D 401/06* (2006.01)
*C07D 401/14* (2006.01)

(52) U.S. Cl.
CPC ......... *C07D 401/06* (2013.01); *C07D 401/14* (2013.01)

(58) Field of Classification Search
CPC ..................... C07D 401/14; C07D 401/06
USPC ..................... 546/268.4, 273.4; 514/338
See application file for complete search history.

(56) References Cited

U.S. PATENT DOCUMENTS

| 4,075,340 | A | 2/1978 | Maffrand |
| 7,566,789 | B2 | 7/2009 | Dorsch et al. |
| 2007/0225282 | A1 | 9/2007 | Player et al. |
| 2009/0181983 | A1 | 7/2009 | Corte |

FOREIGN PATENT DOCUMENTS

| WO | 1999026933 A1 | 6/1999 |
| WO | 2016015593 A1 | 2/2016 |
| WO | 2016018702 A1 | 2/2016 |

OTHER PUBLICATIONS

International Search Report and Written Opinion for PCT/US2015/041646 dated Oct. 15, 2015, 8 pages.
European Search Report for 15827597.4, dated Feb. 19, 2018, 7 pages.

*Primary Examiner* — Patricia L Morris
(74) *Attorney, Agent, or Firm* — Nicole M. Beeler; John C. Todaro

(57) ABSTRACT

The present invention provides a compound of Formula (I) and pharmaceutical compositions comprising one or more said compounds, and methods for using said compounds for treating or preventing thromboses, embolisms, hypercoagulability or fibrotic changes. The compounds are selective Factor XIa inhibitors or dual inhibitors of Factor XIa and plasma kallikrein.

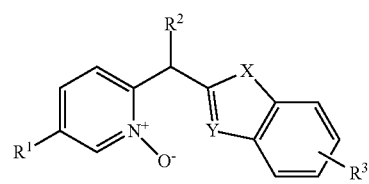

12 Claims, No Drawings

FACTOR XIA INHIBITORS

CROSS REFERENCE TO RELATED APPLICATIONS

This application is a U.S. National Phase application under 35 U.S.C. § 371 of PCT Application No. PCT/US2015/041646 filed Jul. 23, 2015, which claims priority from U.S. Provisional Application Ser. No. 62/029,772, filed Jul. 28, 2014.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commence after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. The activation of factor XIa is a central point of intersection between the two pathways of activation of clotting. Factor XIa has an important role in blood clotting.

Coagulation is initiated when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor 25 XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., Blood, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact ActivationPathway", Hemostasis and Thrombosis, pp. 103-122, Lippincott Williams & Wilkins (2001); Schmaier, A. H., "Contact Activation", Thrombosis and Hemorrhage, pp. 105-128 (1998)). The biological relevance of the contact activation system for thromboembolic 5 diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., J Exp. Med., 202:271-281 (2005); Kleinschmitz et al., J Exp. Med., 203:513-518 (2006)). The fact that factor XI is downstream from factor XIIa, combined with the identical phenotype of the XII and XI deficient mice suggest that the contact activation system could play a major role in factor XI activation in vivo.

Plasma kallikrein is a zymogen of a trypsin-like serine protease and is present in plasma. The gene structure is similar to that of factor XI. Overall, the amino acid sequence of plasma kallikrein has 58% homology to factor XI. Proteolyticactivation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease 15 inhibitors, including alpha 2 macroglobulin and Cl-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R., "Contact Activation Pathway", Hemostasis and Thrombosis, pp. 103-122, Lippincott Williams & Wilkins (2001); Schmaier A. H., "Contact Activation", Thrombosis and Hemorrhage, pp. 105-128 (1998)).

Patients presenting genetic deficiency on Cl-esterase inhibitor suffer from hereditary angioedema (HAE), a lifelong disease that results in intermittent swelling throughout the body, including the hands, feet, face, throat, genitals and gastrointestinal tract. Analysis of blisters arising from acute episodes have been shown to contain high levels of plasma kallikrein, and treatment with a protein-based reversible plasma kallikrein inhibitor, Ecallantide (Kalbitor), has been approved by the FDA for the treatment of acute attacks of HAE (Schneider, L, et al., J. Allergy Clin. Immunol., 120: p. 416 (2007)).

Additionally, the plasma kallikrein-kinin system is abnormally abundant in patients diagnosed with advanced diabetic macular edema (DME). Recent publications have shown that plasma kallikrein contributes to observed retinal vascular leakage and dysfunction in diabetic rodent models (A. Clermont, et al., Diabetes, 60:1590 (2011)), and that treatment with a small molecule plasma kallikrein inhibitor ameliorated the observed retinal vascular permeability and other abnormalities related to retinal blood flow.

Factor XIa inhibitor compounds are described in WO2014160592, WO2013022814, WO 2013022814, WO 2013022818, WO 2013055984, WO2013056034, WO2013056060, WO2013118805. WO2013093484. WO2002042273, WO2002037937, WO2002060894, WO2003015715, WO2004002405, US20040180855, WO2004080971, WO2004094372, US20050228000, US20050282805, WO2005123680, US20090036438, US20120088758, US20060074103, WO2006062972, WO2006076246, US20060154915, US20090062287, US20060183771, WO2007070818, WO2007070816, WO2007070826, WO2008076805, WO2008157162, WO2009114677, WO2011100402, and WO2011100401.

SUMMARY OF THE INVENTION

The present invention relates to compounds of Formula I:

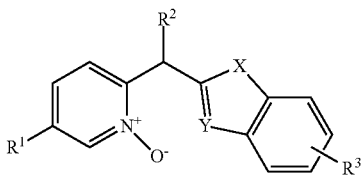

I or pharmaceutically acceptable salts thereof. The compounds of Formula I and pharmaceutically acceptable salts thereof are selective Factor XIa inhibitors or dual inhibitors of Factor XIa and plasma kallikrein, and as such may be useful in the treatment, inhibition or amelioration of one or more disease states that could benefit from inhibition of Factor XIa or plasma kallikrein, including thromboses, embolisms, hypercoaguability or fibrotic changes. The compounds of this invention could further be used in combination with other therapeutically effective agents, including but not limited to, other drugs useful for the treatment of thrombosis, embolisms, hypercoaguability or fibrotic changes. The invention furthermore relates to processes for preparing compounds of Formula I, and pharmaceutical compositions which comprise compounds of Formula I and pharmaceutically acceptable salts thereof.

DETAILED DESCRIPTION OF THE INVENTION

The present invention relates to compounds of Formula I:

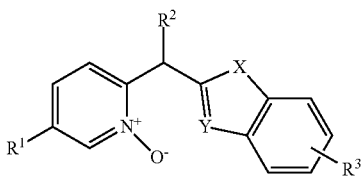

I wherein X is NH, O, S or $CR^4R^5$;
Y is N or $CR^4$;
$R^1$ is aryl, heteroaryl, $C_{3-6}$ cycloalkyl or heterocyclyl, wherein said aryl, heteroaryl, cycloalkyl and heterocyclyl groups are optionally substituted with one to three substituents independently selected from the group consisting of halo, nitro, cyano, oxo, $R^4$, $OR^4$, $(C=O)R^4$, $(C=O)OR^4$, $(C=O)NR^4R^5$, $NR^4R^5$, $NH(C=O)R^4$, $NH(C=O)OR^4$, $C(NH)NR^4R^5$, $C_{3-6}$ cycloalkyl and heteroaryl which is optionally substituted with $R^4$;
$R^2$ is hydrogen or $CH(R^{2a})(R^{2b})$;
$R^{2a}$ is hydrogen, $C_{1-6}$ alkyl, aryl, heteroaryl, $C_{3-6}$ cycloalkyl, heterocyclyl or $(C=O)$heterocyclyl, wherein said alkyl group is optionally substituted with one to three substituents independently selected from the group consisting of halo, hydroxy and cyano, and wherein said aryl, heteroaryl, cycloalkyl and heterocyclyl groups are optionally substituted with one to three substituents independently selected from the group consisting of halo, nitro, cyano, oxo, $R^4$ and $OR^4$;
$R^{2b}$ is hydrogen or $C_{1-6}$ alkyl, which is optionally substituted with one to three substituents independently selected from the group consisting of halo, hydroxy and cyano;
$R^3$ is halo, cyano, $(C=O)OR^4$ or $R^6$;
$R^4$ is hydrogen or $C_{1-6}$ alkyl, which is optionally substituted with one to three groups independently selected from the group consisting of halo and hydroxy;
$R^5$ is hydrogen or $C_{1-6}$ alkyl, which is optionally substituted with one to three groups independently selected from the group consisting of halo and hydroxy;
$R^6$ is aryl, heteroaryl, $C_{3-10}$ cycloalkyl or heterocyclyl, wherein said aryl, heteroaryl, cycloalkyl and heterocyclyl groups are optionally substituted with one to three substituents independently selected from the group consisting of halo, nitro, cyano, oxo, $R^4$, $OR^4$, $(C=O)R^4$, $(C=O)OR^4$, $(C=O)NR^4R^5$, $NR^4R^5$, $NH(C=O)R^4$, $NH(C=O)OR^4$, $SO_2R^4$, $SO_2NR^4R^5$, $NR^4SO_2R^5$ and $PO_3R^4$;
or a pharmaceutically acceptable salt thereof.

An embodiment of the present invention relates to compounds of Formula Ia:

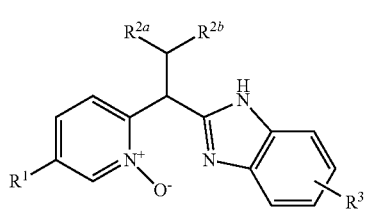

Ia wherein $R^1$ is aryl, heteroaryl, $C_{3-6}$ cycloalkyl or heterocyclyl, wherein said aryl, heteroaryl, cycloalkyl and heterocyclyl groups are optionally substituted with one to three substituents independently selected from the group consisting of halo, nitro, cyano, oxo, $R^4$, $OR^4$, $(C=O)R^4$, $(C=O)OR^4$, $(C=O)OR^4$, $NR^4R^5$, $NH(C=O)R^4$, $NH(C=O)OR^4$, $C(NH)NR^4R^5$, $C_{3-6}$ cycloalkyl and heteroaryl which is optionally substituted with $R^4$;
$R^{2a}$ is hydrogen, $C_{1-6}$ alkyl, aryl, heteroaryl, $C_{3-6}$ cycloalkyl, heterocyclyl or $(C=O)$heterocyl, wherein said alkyl group is optionally substituted with one to three substituents independently selected from the group consisting of halo, hydroxy and cyano, and wherein said aryl, heteroaryl, cycloalkyl and heterocyclyl groups are optionally substituted with one to three substituents independently selected from the group consisting of halo, nitro, cyano, oxo, $R^4$ and $OR^4$;
$R^{2b}$ is hydrogen or $C_{1-6}$ alkyl, which is optionally substituted with one to three substituents independently selected from the group consisting of halo, hydroxy and cyano;

$R^3$ is halo, cyano, (C=O)OR$^4$ or R$^6$;
$R^4$ is hydrogen or $C_{1-6}$ alkyl, which is optionally substituted with one to three groups independently selected from the group consisting of halo and hydroxy;
$R^5$ is hydrogen or $C_{1-6}$ alkyl, which is optionally substituted with one to three groups independently selected from the group consisting of halo and hydroxy;
$R^6$ is aryl, heteroaryl, $C_{3-10}$ cycloalkyl or heterocyclyl, wherein said aryl, heteroaryl, cycloalkyl and heterocyclyl groups are optionally substituted with one to three substituents independently selected from the group consisting of halo, nitro, cyano, oxo, R$^4$, OR$^4$, (C=O)R$^4$, (C=O)OR$^4$, (C=O)NR$^4$R$^5$, NR$^4$R$^5$, NH(C=O)R$^4$, NH(C=O)OR$^4$, SO$_2$R$^4$, SO$_2$NR$^4$R$^5$, NR$^4$SO$_2$R$^5$ and PO$_3$R$^4$;

or a pharmaceutically acceptable salt thereof.

An embodiment of the present invention relates to compounds of Formula Ib:

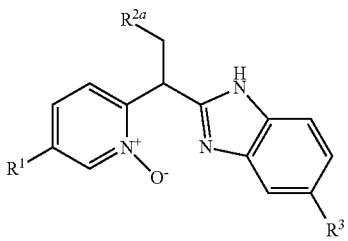

Ib wherein R$^1$ is aryl, heteroaryl, $C_{3-6}$ cycloalkyl or heterocyclyl, wherein said aryl, heteroaryl, cycloalkyl and heterocyclyl groups are optionally substituted with one to three substituents independently selected from the group consisting of halo, nitro, cyano, oxo, R$^4$, OR$^4$, (C=O)R$^4$, (C=O)OR$^4$, (C=O)OR$^4$, NR$^4$R$^5$, NH(C=O)R$^4$, NH(C=O)OR$^4$, C(NH)NR$^4$R$^5$, $C_{3-6}$ cycloalkyl and heteroaryl which is optionally substituted with R$^4$;
$R^{2a}$ is hydrogen, $C_{1-6}$ alkyl, aryl, heteroaryl, $C_{3-6}$ cycloalkyl, heterocyclyl or (C=O)heterocycyl, wherein said alkyl group is optionally substituted with one to three substituents independently selected from the group consisting of halo, hydroxy and cyano, and wherein said aryl, heteroaryl, cycloalkyl and heterocyclyl groups are optionally substituted with one to three substituents independently selected from the group consisting of halo, nitro, cyano, oxo, R$^4$ and OR$^4$;
$R^3$ is halo, cyano, (C=O)OR$^4$ or R$^6$;
$R^4$ is hydrogen or $C_{1-6}$ alkyl, which is optionally substituted with one to three groups independently selected from the group consisting of halo and hydroxy;
$R^5$ is hydrogen or $C_{1-6}$ alkyl, which is optionally substituted with one to three groups independently selected from the group consisting of halo and hydroxy;
$R^6$ is aryl, heteroaryl, $C_{3-10}$ cycloalkyl or heterocyclyl, wherein said aryl, heteroaryl, cycloalkyl and heterocyclyl groups are optionally substituted with one to three substituents independently selected from the group consisting of halo, nitro, cyano, oxo, R$^4$, OR$^4$, (C=O)R$^4$, (C=O)OR$^4$, (C=O)NR$^4$R$^5$, NR$^4$R$^5$, NH(C=O)R$^4$, NH(C=O)OR$^4$, SO$_2$R$^4$, SO$_2$NR$^4$R$^5$, NR$^4$SO$_2$R$^5$ and PO$_3$R$^4$;

or a pharmaceutically acceptable salt thereof.

In an embodiment of the invention, R$^1$ is aryl, which optionally is substituted with one to three substituents independently selected from the group consisting of halo, $C_{3-6}$ cycloalkyl and heteroaryl which is optionally substituted with R$^4$. In a class of the embodiment, R$^1$ is phenyl, which optionally is substituted with one to two substituents independently selected from the group consisting of halo and tetrazolyl. In a class of the embodiment, R$^1$ is phenyl, which optionally is substituted with three halo.

In an embodiment of the invention, R$^2$ is hydrogen. In another embodiment of the invention, R$^2$ is CH(R$^{2a}$)(R$^{2b}$).

In an embodiment of the invention, R$^{2a}$ is aryl, which optionally is substituted with one to three halo. In a class of the embodiment, R$^{2a}$ is phenyl. In another class of the embodiment, R$^{2a}$ is phenyl which is substituted with halo. In another embodiment of the invention, R$^{2a}$ is $C_{3-8}$ cycloalkyl. In a class of the embodiment, R$^{2a}$ is cyclopropyl.

In an embodiment of the invention, R$^{2b}$ is hydrogen.

In an embodiment of the invention, R$^3$ is halo, cyano or (C=O)OR$^4$. In a class of the invention, R$^3$ is halo. In another class of the invention, R$^3$ is cyano. In another class of the invention, R$^3$ is (C=O)OR$^4$.

In an embodiment of the invention, R$^6$ is aryl, which is optionally substituted with one to three substituents independently selected from the group consisting of halo, nitro, cyano, oxo, R$^4$, OR$^4$, (C=O)R$^4$, (C=O)OR$^4$, (C=O)NR$^4$R$^5$, NR$^4$R$^5$, NH(C=O)R$^4$, NH(C=O)OR$^4$, SO$_2$R$^4$, SO$_2$NR$^4$R$^5$, NR$^4$SO$_2$R$^5$ and PO$_3$R$^4$. In a class of the invention, R$^6$ is phenyl, which is optionally substituted with one to three substituents independently selected from the group consisting of NH(C=O)OR$^4$, (C=O)OR, and SO$_2$R$^4$. In another embodiment of the invention, R$^6$ is heterocycyl, which is optionally substituted with one to three substituents independently selected from the group consisting of halo, nitro, cyano, oxo, R$^4$, OR$^4$, (C=O)R$^4$, (C=O)OR$^4$, (C=O)NR$^4$R$^5$, NR$^4$R$^5$, NH(C=O)R$^4$, NH(C=O)OR$^4$, SO$_2$R$^4$, SO$_2$NR$^4$R$^5$, NR$^4$SO$_2$R$^5$ and PO$_3$R$^4$. In a class of the embodiment of the invention, R$^6$ is heterocycyl, which is optionally substituted with (C=O)NR$^4$R$^5$.

The present invention also relates to compounds of Formula I:

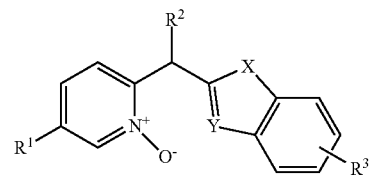

I wherein X is NH, O, S or CR$^4$R$^5$;
Y is N or CR$^4$;
R$^1$ is aryl, heteroaryl, $C_{3-6}$ cycloalkyl or heterocyclyl, wherein said aryl, heteroaryl, cycloalkyl and heterocyclyl groups are optionally substituted with one to three substituents independently selected from the group consisting of halo, nitro, cyano, oxo, R$^4$, OR$^4$, (C=O)R$^4$, (C=O)OR$^4$, NR$^4$R$^5$, NH(C=O)R$^4$, NH(C=O)OR$^4$, C(NH)NR$^4$R$^5$, $C_{3-6}$ cycloalkyl and heteroaryl which is optionally substituted with R$^4$;
R$^2$ is hydrogen or CH(R$^{2a}$)(R$^{2b}$);
$R^{2a}$ is hydrogen, $C_{1-6}$ alkyl, aryl, heteroaryl, $C_{3-6}$ cycloalkyl or heterocyclyl, wherein said alkyl group is optionally substituted with one to three substituents independently selected from the group consisting of halo, hydroxy and cyano, and wherein said aryl, heteroaryl, cycloalkyl and heterocyclyl groups are optionally substituted with one to three substituents independently selected from the group consisting of halo, nitro, cyano, oxo, R$^4$ and OR$^4$;

$R^{2b}$ is hydrogen or $C_{1-6}$ alkyl, which is optionally substituted with one to three substituents independently selected from the group consisting of halo, hydroxy and cyano;

$R^3$ is halo, cyano, (C=O)OR$^4$ or $R^6$;

$R^4$ is hydrogen or $C_{1-6}$ alkyl, which is optionally substituted with one to three groups independently selected from the group consisting of halo and hydroxy;

$R^5$ is hydrogen or $C_{1-6}$ alkyl, which is optionally substituted with one to three groups independently selected from the group consisting of halo and hydroxy;

$R^6$ is aryl, heteroaryl, $C_{3-10}$ cycloalkyl or heterocyclyl, wherein said aryl, heteroaryl, cycloalkyl and heterocyclyl groups are optionally substituted with one to three substituents independently selected from the group consisting of halo, nitro, cyano, oxo, $R^4$, OR$^4$, (C=O)R$^4$, (C=O)OR$^4$, (C=O)NR$^4$R$^5$, NR$^4$R$^5$, NH(C=O)R$^4$, NH(C=O)OR$^4$, SO$_2$R$^4$, SO$_2$NR$^4$R$^5$, NR$^4$SO$_2$R$^5$ and PO$_3$R$^4$;

or a pharmaceutically acceptable salt thereof.

Reference to the preferred classes and subclasses set forth above is meant to include all combinations of particular and preferred groups unless stated otherwise.

Specific embodiments of the present invention include, but are not limited to the compounds identified herein as Examples 1 to 28, or pharmaceutically acceptable salts thereof.

Also included within the scope of the present invention is a pharmaceutical composition which is comprised of a compound of Formula I, Formula Ia or Formula Ib as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention also includes compositions for inhibiting loss of blood platelets, inhibiting formation of blood platelet aggregates, inhibiting formation of fibrin, inhibiting thrombus formation, inhibiting embolus formation, treating inflammatory disorders, treating diabetic retinopathy and treating hereditary angioedema in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes compositions for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor XIa inhibitors and may have therapeutic value in, for example, preventing coronary artery disease. The compounds are selective Factor XIa inhibitors or dual inhibitors of Factor XIa and plasma kallikrein.

It will be understood that, as used herein, references to the compounds of structural Formula I, Formula Ia and Formula Ib are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Also included are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

If the compounds of Formula I, Formula Ia or Formula Ib simultaneously contain acidic and basic groups in the molecule the invention also includes, in addition to the salt forms mentioned, inner salts or betaines (zwitterions).

The present invention encompasses all stereoisomeric forms of the compounds of Formula I, Formula Ia and Formula Ib. Centers of asymmetry that are present in the compounds of Formula I, Formula Ia and Formula Ib can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. When a particular configuration is depicted, that entantiomer (either (R) or (S), at that center) is intended. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I, Formula Ia or Formula Ib or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^4$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I, Formula Ia and Formula Ib are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Reference to the compounds of this invention as those of a specific formula or embodiment, e.g., Formula I, Formula Ia or Formula Ib or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, the term "alkyl" is intended to include both branched- and straight-chain saturated aliphatic hydrocarbon groups having the specified number of carbon atoms. Commonly used abbreviations for alkyl groups are used throughout the specification, e.g. methyl, may be represented by conventional abbreviations including "Me" or $CH_3$ or a symbol that is an extended bond as the terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. For example, the structures

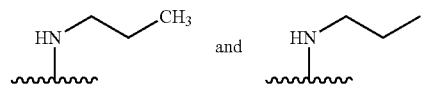

have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Except where noted, the term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on.

Except where noted, the term "halogen" or "halo" means fluorine, chlorine, bromine or iodine.

Except where noted, the term "heteroaryl", as used herein, represents a stable monocyclic or bicyclic ring system of up to 10 atoms in each ring, wherein at least one ring is aromatic, and at least one ring contains from 1 to 4 heteroatoms selected from the group consisting of O, N and S. Bicyclic heteroaryl ring systems include fused ring systems, where two rings share two atoms, and spiro ring systems, where two rings share one atom. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, tetrahydroquinoline and 3-oxo-3,4dihydro-2Nbenzo[b][1,4]thiazine. If the heteroaryl contains nitrogen atoms, it is understood that the corresponding N-oxides thereof are also encompassed by this definition.

Except where noted, the term "heterocycle" or "heterocyclyl" as used herein is intended to mean a stable nonaromatic monocyclic or bicyclic ring system of up to 10 atoms in each ring, unless otherwise specified, containing from 1 to 4 heteroatoms selected from the group consisting of O, N, S, SO, or $SO_2$. Bicyclic heterocyclic ring systems include fused ring systems, where two rings share two atoms, and spiro ring systems, where two rings share one atom. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

Except where noted, the term "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl and indanyl.

"Celite®" (Fluka) diatomite is diatomaceous earth, and can be referred to as "celite".

Except where noted herein, structures containing substituent variables such as variable "R" below:

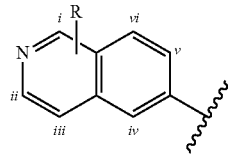

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also includes derivatives of the compounds of Formula I, Formula Ib and Formula Ib, acting as prodrugs and solvates. Prodrugs, following administration to the patient, are converted in the body by normal metabolic or chemical processes, such as through hydrolysis in the blood, to the compound of Formula I, Formula Ia or Formula Ib. Such prodrugs include those that demonstrate enhanced bioavailability, tissue specificity, and/or cellular delivery, to improve drug absorption of the compound of Formula I, Formula Ia or Formula Ib. The effect of such prodrugs may result from modification of physicochemical properties such as lipophilicity, molecular weight, charge, and other physicochemical properties that determine the permeation properties of the drug.

The preparation of pharmaceutically acceptable salts from compounds of the Formula I, Formula Ia and Formula Ib capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula I, Formula Ia and Formula Ib form stable alkali metal, alkaline earth metal or optionally substituted ammonium salts. If the compounds of the Formula I, Formula Ia and Formula Ib have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments containing at least one compound of the Formula I, Formula Ia or Formula Ib and/or of a pharmaceutically acceptable salt of the compound of the Formula I, Formula Ia or Formula Ib and/or an optionally stereoisomeric form of the compound of the Formula I, Formula Ia or Formula Ib or a pharmaceutically acceptable salt of the stereoisomeric form of the compound of Formula I, Formula Ia or Formula Ib, together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, humans, sheep, horses, cattle, pigs, dogs, cats, rats, and mice.

Factor XIa or dual Factor XIa/plasma kallikrein inhibition are useful not only in the anticoagulant therapy of individuals having thrombotic conditions, but are useful whenever inhibition of blood coagulation is required such as to prevent coagulation of stored whole blood and to prevent coagulation in other biological samples for testing or storage. Thus, the Factor XIa or dual Factor XIa/plasma kallikrein inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

The compounds of the invention may also be kallikrein inhibitors and especially useful for treatment of hereditary angioedema.

Examples of devices that come into contact with blood include vascular grafts, stents, orthopedic prosthesis, cardiac prosthesis, and extracorporeal circulation systems.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor XIa inhibitors or dual Factor XIa/plasma kallikrein inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor XIa inhibitors or dual Factor XIa/plasma kallikrein inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the Factor XIa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of the Formula I, Formula Ia and Formula Ib can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor XIa inhibitors or dual Factor XIa/plasma kallikrein inhibitors can also be co-administered with suitable anticoagulants, including, but not limited to, other Factor XIa inhibitors, thrombin inhibitors, thrombin receptor antagonists, factor VIIa inhibitors, factor Xa inhibitors, factor IXa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor XIa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazosin, prazosin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin and remogliflozin), and SGLT-3; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor XIa inhibitors or Factor XIa/plasma kallikrein inhibitors of the invention in combination with other suitable anti-platelet agents, anticoagulation agents, or thrombolytic agents may be the same as those doses of Factor XIa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e., prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, Adv. Enzyme Regul. 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

List of Abbreviations

ACN=acetonitrile
AcOH or HOAc=acetic acid
aq=aqueous
DMF=dimethylformamide
DCM=dichloromethane
DIPEA=N,N-Diisopropylethylamine
EtOAc=ethyl acetate
EtOH=ethanol
h or hr=hour
Hex=Hexanes
HPLC=High Pressure Liquid Chromatography
RP HPLC=Reverse Phase
LCMS=Liquid chromatography-mass spectrometry
LHMDS=lithium hexamethyldisilazide
LiOH=lithium hydroxide
Me=methyl
MeOH=methanol
min=minute
MS=mass spectrometry
mCPBA=meta-chloroperoxybenzoic acid
NCS=N-chlorosuccinimide
rt or RT=room temperature
THF=tetrahydrofuran
SEM=2-(trimethylsilyl)ethoxymethyl
SFC=supercritical fluid chromatography
SM=Starting material
TFA=Trifluoroacetic acid
Vac=Vacuum
HATU=2-(1H-7-Azabenzotriazol-1-yl)-1,1,3,3-tetramethyluronium hexafluorophosphate Methanaminium Also, TLC is thin layer chromatography; Ts is tosyl; UV is ultraviolet; W is watts; wt. % is percentage by weight; xg is times gravity; $\alpha_D$ is the specific rotation of polarized light at 589 nm; ° C. is degrees Celsius; % w/v is percentage in weight of the former agent relative to the volume of the latter agent.

"F11a IC50" is Factor XIa IC50 and "PK IC50" is Plasma Kallekrein IC50.

LCMS conditions: column: SUPELCO Ascentis Express C18 3×100 mm, 2.7 µm.
Solvent system: A—0.05% TFA in water and B— 0.05% TFA in Acetonitrile.
Gradient condition: 10% B to 99% B in 3.5 min.

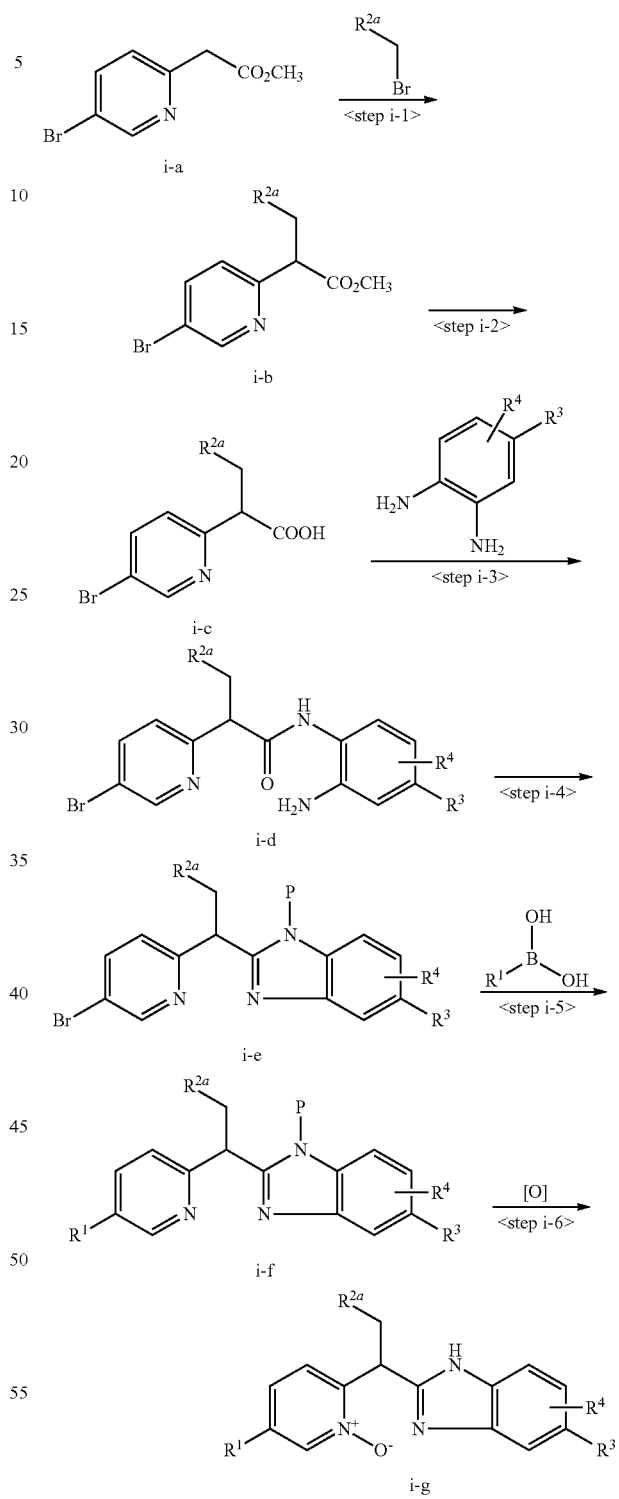

SCHEME 1

<Step i-1>
A compound represented by formula (i-b) can be produced by allowing the commercially available (i-a) to react with a properly substituted alkylating reagent such as alkylhalide, alkylmethanasulfonate, and alkyl-p-toluenesulfonate by a well-known process or a process similar to that described in published documents (Stille, J. K., Angew.

Chem. 1986, Vol 98, pp 504, for example), in the presence of a base such as lithium bis(trimethylsilyl)amide (LH-MDS), lithium diisopropylamide (LDA), or sodium hydride in a solvent which is inactive to the reaction such as tetrahydrofuran or toluene at a temperature in the range of −78° C. to reflux temperature.

<Step i-2>

A compound represented by formula (i-c) can be produced by allowing the suitably substituted (i-b) to react with an inorganic or organic base such as lithium hydroxide, sodium hydroxide, or sodium tert-butoxide by a well-known process or a process similar to that described in published documents (*Org. Lett.*, 2004, 3, 2835-2838; *Org. Synth. Coll.* 1990, Vol. 7: pp 168 for example) in an aqueous solvent containing water and organic co-solvent such as methanol, acetonitrile, and tetrahydrofuran.

<Step i-3>

A compound represented by formula (i-d) can be produced by allowing acid (i-c) to react with a substituted diamine by a well-known method or a process similar to that described in published documents (for example, Organic synthesis IV, Acids, amino acids, and peptides, pp. 191-309, 1992, Maruzen Co., Ltd.), in the presence of a condensing agent such as 1,3-dicyclohexylcarbodiimide (DCC), 1-ethyl-3-(3'-dimethylaminopropyl)carbodiimide hydrochloride (WSC.HCl or EDC HCl), O-(7-azabenzotriazol-1-yl)-N,N,N',N'-tetramethyluronium hexafluorophosphate (HATU), benzotriazol-1-yloxy tris(dimethylamino)phosphonium hexafluorophosphate (BOP reagent), or bis(2-oxo-3-oxazolidinyl)phosphinic chloride (BOP-Cl), in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethylformamide, or an alcoholic solvent, e.g., methanol, ethanol, or 2-propanol, in the presence or absence of a base such as triethylamine or N,N-diisopropylethyl amine at a temperature in the range of 0° C. to the solvent reflux temperature.

<Step i-4>

A compound represented by formula (i-e) can be produced by subjecting a compound represented by formula (i-d) to proper cyclization conditions similar to that described in published documents (for example, Bioorganic & Medicinal Chemistry (2006), 14(13), 4490-4518). This reaction is commonly performed in high boiling solvents, such as acetic acid, at elevated temperatures, commonly between 70° C. and the boiling temperature of the solvent, commonly for 2-16 h. Upon completion of cyclization, the reaction mixture is generally treated with an acylating or alkylating agent represented by formula P-X where P is a protection group and X is a halogen. Typical reagents in the form of P-X include (2-Chloromethoxyethyl) trimethylsilane, Chloromethyl 2-trimethylsilylethyl ether (SEM-Cl), toluene sulfonyl chloride, and benzyl chloroformate (Cbz-Cl).

<Step i-5>

A compound represented by formula (i-f) can be produced by a method commonly referred to as the Suzuki coupling reaction. Compounds of type (i-f) can be treated with an aryl- or heteroaryl-boronic acid of type $R^1$—$B(OH)_2$, or alternatively, an aryl- or heteroarylboronate of type $R^1$—$B(OR)_2$, in the presence of a suitable palladium catalyst, such as [1,1'-bis(diphenylphosphino)ferrocene]-dichloropalladium(II), or tetrakis(triphenylphosphine) palladium (0), or the like, and a mild base, such as sodium carbonate, sodium phosphate tribasic, or the like (*Pure Appl. Chem.* 1991, 63, 419-422). The reaction is usually performed in a suitable degassed aqueous mixture of inert organic solvents, such as toluene, ethanol or dioxane, at elevated temperatures, generally between 70° C. and the boiling temperature of the solvent mixture, for a period of 3-24 h. Alternatively, those skilled in the art can perform the Suzuki reaction described above in a suitable vessel that enables heating in a microwave reactor to superheated reaction temperatures that can reduce reaction times to between 1 min and 1 h. Recently, conditions suitable for performing Suzuki reactions at room temperature have been published (for example, see: *J. Am. Chem. Soc.* 2000, 122, 4020-4028, and references therein).

<Step i-6>

A compound represented by formula (i-g) can be produced by allowing the suitably substituted pyridine analog (i-f) to react with an oxidizing reagent commonly referred to as a peroxide, such as hydrogen peroxide, meta-chloroperbenzoic acid, oxone, dimethyldioxirane, and peracetic acid. Such a process or processes similar to that are described in published documents (Stuart Warren and Paul Wyatt (2008). *Organic synthesis: The Disconnection Approach* (2nd ed.) Oxford: Wiley-Blackwell. p. 54 for example). Upon completion of oxidation, the protection group(s) are removed by treating the compound under well established deprotection conditions corresponding to the protection group such as HCl, TFA, NaOH and $H_2$/Pd.

Examples 1, 2 and 3

2-(1-(5-Carboxy-1H-benzo[d]imidazol-2-yl)-2-phenylethyl)-5-(3-chloro-2,6-difluorophenyl)pyridine 1-oxide (Example 1)

(S)-2-(1-(5-Carboxy-1H-benzo[d]imidazol-2-yl)-2-phenylethyl)-5-(3-chloro-2,6-difluorophenyl)pyridine 1-oxide (Example 2) and (R)-2-(1-(5-Carboxy-1H-benzo[d]imidazol-2-yl)-2-phenylethyl)-5-(3-chloro-2,6-difluorophenyl)pyridine 1-oxide (Example 3)

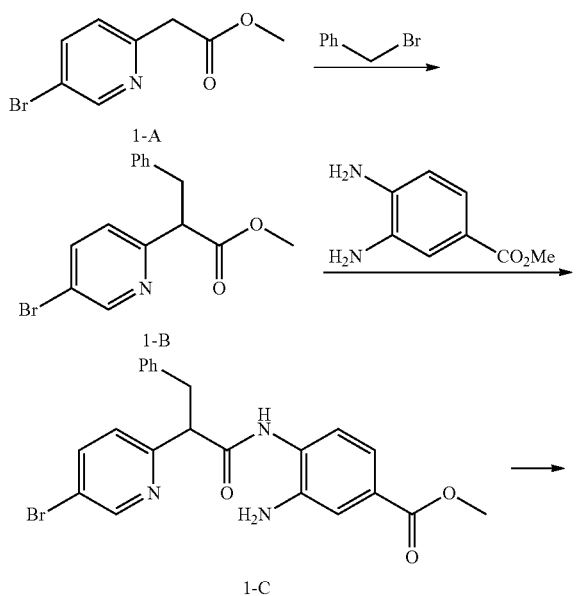

-continued

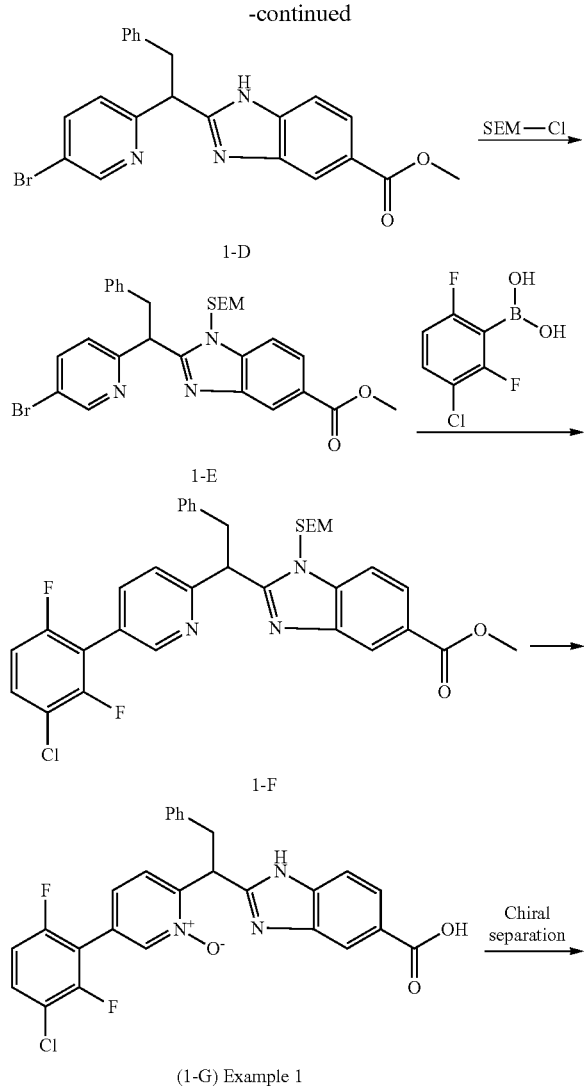

(1-G) Example 1

Example 2 (S)
Example 3 (R)

Step 1. Methyl 2-(5-bromopyridin-2-yl)-3-phenyl-propanoate (1-B)

To a solution of methyl 2-(5-bromopyridin-2-yl)acetate (1-A, 1 g, 4.35 mmol) in THF (20 mL) was added LHMDS (4.35 mL, 4.35 mmol, 1M) at −78° C. The mixture was stirred at −78° C. for 2 hrs. (Bromomethyl)benzene (0.743 g, 4.35 mmol) was added slowly. Next, the cold bath was removed and the mixture was stirred at room temperature for 2 hrs. The reaction mixture was diluted with EtOAc, washed with water, brine and dried over $Na_2SO_4$. The solvent was removed in vacuo. The residue was purified by column chromatography on silica gel, eluting with EtOAc/hexane to give the desired product 1-B. $^1$H NMR (500 MHz, $CDCl_3$) δ: 3.24 (1H, dd), 3.45 (1H, dd), 3.66 (3H, s), 4.09 (1H, t), 7.12-7.09 (4H, m), 7.24-7.12 (2H, m), 7.73 (1H, dd), 8.65 (1H, d).

Step 2. Methyl 4-amino-3-(2-(5-bromopyridin-2-yl)-3-phenylpropanamido)benzoate (1-C)

To a solution of methyl 2-(5-bromopyridin-2-yl)-3-phenylpropanoate (300 mg, 0.937 mmol) (1-B) in MeOH (10 ml) was added aq. LiOH (1.405 ml, 1.405 mmol, 1M). The reaction mixture was heated at 50° C. for 30 min. The solvent was removed under vacuum and dried by azeotrope with toluene twice. The above intermediate acid was dissolved in DMF (10 mL). Methyl 3,4-diaminobenzoate (156 mg, 0.937 mmol) and HATU (356 mg, 0.937 mmol) were added. It was stirred at rt for 30 min. The mixture was diluted with water and extracted with EtOAc. The organic layer was washed with brine and dried over $Na_2SO_4$. The solvent was removed in vacuo. The residue was purified by column chromatography on silica gel, eluting with EtOAc/hexane to give the desired product (1-C). $^1$H NMR (500 MHz, $CDCl_3$) δ: 3.26 (1H, dd), 3.50 (1H, dd), 3.83 (3H, s), 4.13-4.07 (1H, m), 4.22 (2H, s), 6.68 (1H, d), 7.08 (3H, t), 7.21 (3H, m), 7.74-7.71 (3H, m), 8.65 (1H, d), 9.02 (1H, s).

Step 3. Methyl 2-(1-(5-bromopyridin-2-yl)-2-phenylethyl)-1H-benzo[d]imidazole-5-carboxylate (1-D)

A solution of methyl 4-amino-3-(2-(5-bromopyridin-2-yl)-3-phenylpropanamido)benzoate (1-C) (400 mg, 0.880 mmol) in HOAc (6 ml) was heated at 70° C. for 3 hrs. Solvent was removed. The residue was partitioned between EtOAc and saturated $NaHCO_3$ (aq.). The organic layer was washed with brine, dried ($MgSO_4$), filtered and the solvent was evaporated under reduced pressure to give the crude material (1-D) which was used as is in the next step. MS (ESI) m/z 438 (M+H)

Step 4. Methyl 2-(1-(5-bromopyridin-2-yl)-2-phenylethyl)-1-((2-(trimethylsilyl)ethoxy)methyl)-1H-benzo[d]imidazole-5-carboxylate (1-E)

To a solution of methyl 2-(1-(5-bromopyridin-2-yl)-2-phenylethyl)-1H-benzo[d]imidazole-5-carboxylate (1-D) (0.38 g, 0.871 mmol) in $CH_2Cl_2$ (4 ml) was added DIPEA (0.304 ml, 1.742 mmol) followed by addition of SEM-Cl (0.185 ml, 1.045 mmol) at 0° C. It was stirred at 0° C. for 1 hr. The reaction mixture was diluted with water, extracted by EtOAc. The organic layer was washed with brine and dried over $Na_2SO_4$. Solvent was removed under reduced pressure. The residue was purified by column chromatography on silica gel, eluting with EtOAc/hexane to give the desired product (1-E). $^1$H NMR (500 MHz, $CDCl_3$) δ: −0.11 (9H, s), 0.77-0.65 (2H, m), 3.27-3.19 (2H, m), 3.58 (1H, td), 3.85 (1H, m), 3.95 (3H, s), 4.88-4.83 (1H, m), 5.31 (1H, dd), 5.48 (1H, dd), 7.18-7.14 (3H, m), 7.39 (2H, dd), 7.73 (2H, dd), 7.85 (1H, d), 8.01 (2H, dd), 8.12 (1H, s), 8.57 (1H, d).

Step 5. Methyl 2-(1-(5-(3-chloro-2,6-difluorophenyl)pyridin-2-yl)-2-phenylethyl)-1-((2-(trimethylsilyl)ethoxy)methyl)-1H-benzo[d]imidazole-5-carboxylate (1-F)

To a mixture of methyl 2-(1-(5-bromopyridin-2-yl)-2-phenylethyl)-1-((2-(trimethylsilyl)ethoxy)methyl)-1H- benzo[d]imidazole-5-carboxylate (1-E) (86 mg, 0.152 mmol), (3-chloro-2,6-difluorophenyl)boronic acid (44 mg, 0.228 mmol), palladium(II) acetate/1,1'-bis(di-t-butylphosphino)ferrocene/potassium phosphate admixture (28 mg, 0.03 mmol) in THF (2 ml) was added potassium phosphate tribasic aq. solution (0.3 ml, 0.6 mmol, 2M) in a microwave tube. The reaction tube was sealed, degassed and refilled with $N_2$. The mixture was heated at 100° C. by microwave for 1 hr. The reaction mixture was diluted with water, extracted with EtOAc, the organic was washed with brine, and dried over $Na_2SO_4$. The solvent was removed in vacuo. The residue was purified by column chromatography on silica gel, eluting with EtOAc/hexane to give the product (1-F). $^1$H NMR (500 MHz, $CDCl_3$) δ: −0.12 (9H, d), 0.77-0.67 (2H, m), 0.91-0.87 (1H, m), 3.22-3.17 (1H, m), 3.31-3.23 (2H, m), 3.67-3.63 (1H, m), 3.96 (3H, s), 4.99 (1H, b), 5.37 (1H, b), 5.56 (1H, b), 7.00 (1H, dd), 7.22-7.17 (6H, m), 7.44-7.39 (2H, m), 7.75 (1H, s), 8.03 (1H, t,) 8.15 (1H, s), 8.61 (1H, s).

Step 6. 2-(1-(5-Carboxy-1H-benzo[d]imidazol-2-yl)-2-phenylethyl)-5-(3-chloro-2,6-difluorophenyl)pyridine-1-oxide (1-G)

To a solution of methyl 2-(1-(5-(3-chloro-2,6-difluorophenyl)pyridin-2-yl)-2-phenylethyl)-1-((2-(trimethylsilyl)ethoxy)methyl)-1H-benzo[d]imidazole-5-carboxylate (1-F) (60 mg, 0.095 mmol) in MeOH (1 ml) was added $H_2O_2$ (0.083 mL, 0.946 mmol) followed by addition of methyltrioxorhenium(VII) (12 mg, 0.047 mmol). It was stirred at rt for 1 hr. The mixture was washed with $NaHSO_3$ (10% aq.), brine and concentrated to give the crude pyridine N-Oxide product. The above residue was dissolved in MeOH (1 ml). LiOH (aq.) solution (0.3 ml, 0.300 mmol, 1M) was added. The reaction mixture was heated at 50° C. for 30 min. LCMS showed the hydrolyzed acid intermediate. Solvent was removed under reduced pressure. The residue was then dissolved in $CH_2Cl_2$ (0.5 ml) and TFA (0.5 ml, 6.49 mmol) was added. The mixture was heated at 50° C. for 1 hr. The deprotection of the SEM group was completed. The solvent was removed. The residue was redissolved in 1 ml ACN and 0.5 ml $H_2O$. The solution was lyopholyzed to give the product (1-G) (Example 1). 2-(1-(5-Carboxy-1H-benzo[d]imidazol-2-yl)-2-phenylethyl)-5-(3-chloro-2,6-difluorophenyl)pyridine-1-oxide (1-G) was resolved by SFC with a chiral column (OD-H) to give (S)-2-(1-(5-carboxy-1H-benzo[d]imidazol-2-yl)-2-phenylethyl)-5-(3-chloro-2,6-difluorophenyl)pyridine 1-oxide (Example 2) and (R)-2-(1-(5-carboxy-1H-benzo[d]imidazol-2-yl)-2-phenylethyl)-5-(3-chloro-2,6-difluorophenyl)pyridine 1-oxide (Example 3). $^1$H NMR (500 MHz, acetone-$d_6$) δ: 3.68 (1H, dd), 3.78 (1H, dd), 5.46 (1H, m), 7.14 (1H, m), 7.22 (6H, m), 7.26 (1H, m), 7.37 (3H, m), 7.51 (1H, dd), 7.70 (1H, m,) 7.81 (1H, m), 7.92 (1H, m), 8.54 (1H, s).

Examples 4, 5 and 6

2-(1-(5-Carboxy-1H-benzo[d]imidazol-2-yl)-2-phenylethyl)-5-(5-chloro-2-(1H-tetrazol-1-yl)phenyl)pyridine 1-oxide (Example 4) and (S)-2-(1-(5-Carboxy-1H-benzo[d]imidazol-2-yl)-2-phenylethyl)-5-(5-chloro-2-(1H-tetrazol-1-yl)phenyl)pyridine 1-oxide (Example 5) and (R)-2-(1-(5-Carboxy-1H-benzo[d]imidazol-2-yl)-2-phenylethyl)-5-(5-chloro-2-(1H-tetrazol-1-yl)phenyl)pyridine 1-oxide (Example 6)

1-B ⟶

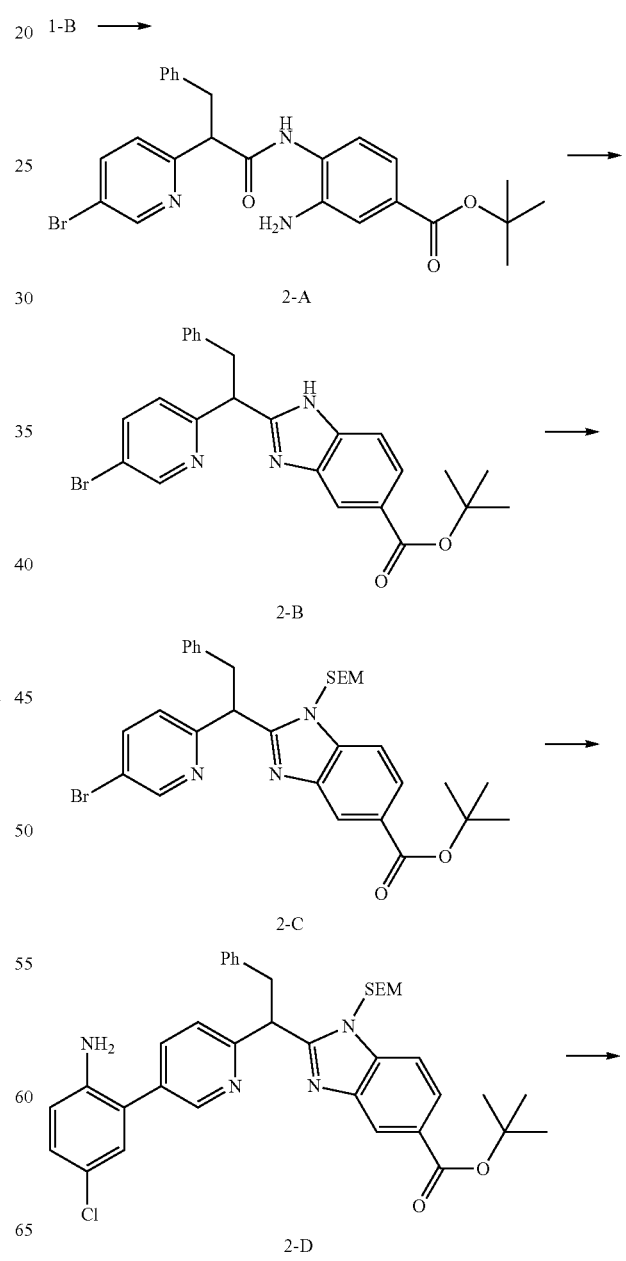

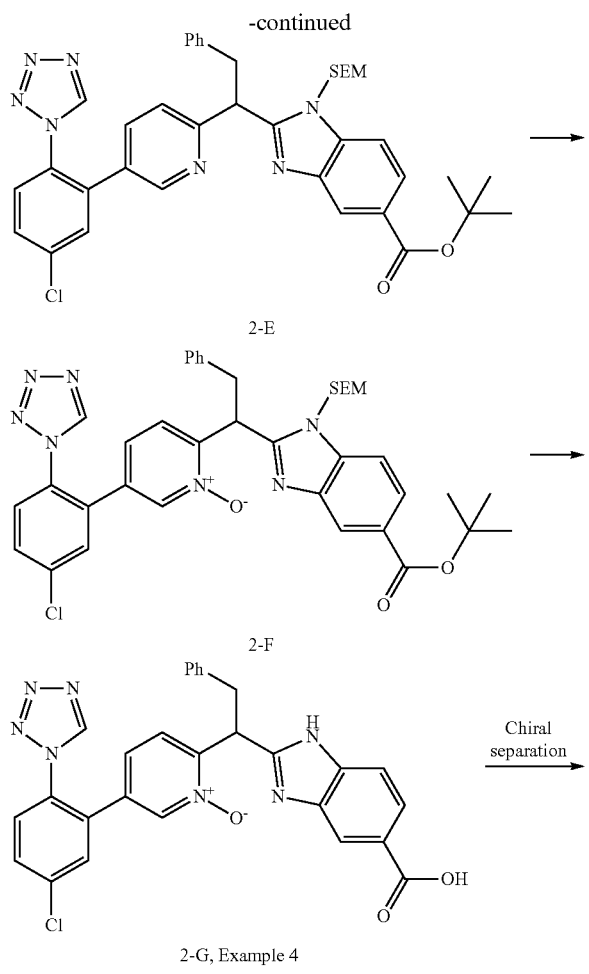

2-E

2-F

2-G, Example 4

Chiral separation →

Example 5 (S)
Example 6 (R)

Step 1. tert-Butyl 4-amino-3-(2-(5-bromopyridin-2-yl)-3-phenylpropanamido)benzoate (2-A)

To a solution of ethyl 2-(5-bromopyridin-2-yl)-3-phenylpropanoate (1-B) (600 mg, 1.795 mmol) in MeOH (10 ml) was added LiOH aqueous solution (1M) (2.69 ml, 2.69 mmol). The mixture was heated at 50° C. for 15 minutes. The solvent was removed under vacuum and dried by azeotrope with toluene twice. The above acid intermediate was dissolved in DMF (10.00 ml). tert-Butyl 3,4-diaminobenzoate (374 mg, 1.795 mmol) and HATU (683 mg, 1.795 mmol) were added. It was stirred at room temperature for 30 minutes. The mixture was diluted with water and extracted with EtOAc. The organic layer was washed with brine and dried over $Na_2SO_4$, and solvent was removed in vacuo. The residue was purified by column chromatography on silica gel, eluting with EtOAc/hexane to give the desired product 2-A. $^1$H NMR (500 MHz, $CDCl_3$) δ: 1.56 (9H, s), 3.28 (1H, dd), 3.53 (1H, dd), 4.07 (1H, m), 6.71 (1H, d), 7.05 (1H, d), 7.10 (1H d), 7.25 (3H, m), 7.65 (1H, s), 7.70 (1H, d), 7.74 (1H, d), 8.70 (1H, s), 8.91 (1H, s).

Step 2. tert-Butyl 2-(1-(5-bromopyridin-2-yl)-2-phenylethyl)-1H-benzo[d]imidazole-5-carboxylate (2-B)

A solution of tert-Butyl 4-amino-3-(2-(5-bromopyridin-2-yl)-3-phenylpropanamido)benzoate (2-A) (200 mg, 0.403 mmol) in HOAc (15 ml) was heated at 70° C. for 3 hours. The solvent was removed. The residue was partitioned between EtOAc and saturated $NaHCO_3$ (aq.). The organic layer was washed with brine, dried ($MgSO_4$), filtered, and the solvent was evaporated under reduced pressure. The residue was purified by column chromatography on silica gel, eluting with EtOAc/hexane to give the desired product (2-B). $^1$H NMR (500 MHz, $CDCl_3$) δ: 1.62 (9H, s), 3.40 (1H, dd), 3.56 (1H, dd), 4.84 (1H, m), 6.96 (3H, m), 7.02 (1H, d), 7.15 (3H m), 7.58 (1H, d), 7.67 (1H, d), 7.94 (1H, d), 8.29 (1H, s), 8.70 (1H, s).

Step 3. tert-Butyl 2-(1-(5-bromopyridin-2-yl)-2-phenylethyl)-1-((2-(trimethylsilyl)ethoxy)methyl)-1H-benzo[d]imidazole-5-carboxylate (2-C)

To a solution of tert-butyl 2-(1-(5-bromopyridin-2-yl)-2-phenylethyl)-1H-benzo[d]imidazole-5-carboxylate (2-B) (170 mg, 0.355 mmol) in $CH_2Cl_2$ (3 ml) was added DIPEA (0.124 ml, 0.711 mmol) followed by addition of SEM-Cl (0.076 ml, 0.426 mmol) at room temperature. It was stirred for 1 hour. The reaction mixture was diluted with water, and extracted with EtOAc. The organic layer was washed with brine and dried over $Na_2SO_4$. The solvent was removed under reduced pressure. The residue was purified by column chromatography on silica gel, eluting with EtOAc/hexane to give the desired product (2-C). $^1$H NMR (500 MHz, $CDCl_3$) δ: −0.11 (9H, s), 0.68 (2H, m), 1.62 (9H, s), 3.18 (1H, m), 3.24 (1H, m), 3.58 (1H, m), 3.84 (1H, m), 4.85 (1H, m), 5.29 (1H, dd), 5.46 (1H, dd), 7.18-7.14 (5H, m), 7.39 (2H, m), 7.71 (1H, dd), 7.82 (1H, d), 7.96 (1H, d), 8.06 (1H, s), 8.57 (1H, s).

Step 4. tert-Butyl 2-(1-(5-(2-amino-5-chlorophenyl)pyridin-2-yl)-2-phenylethyl)-1-((2-(trimethylsilyl)ethoxy)methyl)-1H-benzo[d]imidazole-5-carboxylate (2-D)

A reaction mixture of 4-chloro-2-(4,4,5,5-tetramethyl-1,3,2-dioxaborolan-2-yl)aniline (45.8 mg, 0.181 mmol), tert-butyl 2-(1-(5-bromopyridin-2-yl)-2-phenylethyl)-1-((2-(trimethylsilyl)ethoxy)methyl)-1H-benzo[d]imidazole-5-carboxylate (2-C) (110 mg, 0.181 mmol), $PdCl_2$(dppf) (26.4 mg, 0.036 mmol) and CsF (82 mg, 0.542 mmol) in dioxane (1.5 ml) was degassed and refilled with $N_2$. It was heated at 110° C. for 1 hour in an oil bath with strong stirring. The reaction mixture was diluted with water, extracted with EtOAc, the organic was washed with brine, and dried over $Na_2SO_4$. The solvent was removed in vacuo. The residue was purified by column chromatography on silica gel, eluting with EtOAc/hexane to give the product (2-D). $^1$H NMR (500 MHz, $CDCl_3$) δ: −0.12 (9H, s), 0.79-0.64 (2H, m), 1.62 (9H, s), 3.32-3.18 (2H, m), 3.72-3.57 (2H, m), 3.91 (1H, m), 4.96 (1H, m), 5.32 (1H, dd), 5.56 (1H, dd), 6.70 (1H, d), 7.03 (1H, s), 7.23-7.12 (6H, m), 7.39 (1H, m), 7.59 (1H, m), 7.72 (1H, d), 7.84 (1H, d), 7.96 (1H, d,) 8.07 (1H, s), 8.57 (2H, m).

Step 5. tert-Butyl 2-(1-(5-(5-chloro-2-(1H-tetrazol-1-yl)phenyl)pyridin-2-yl)-2-phenylethyl)-1-((2-(trimethylsilyl)ethoxy)methyl)-1H-benzo[d]imidazole-5-carboxylate (2-E)

A reaction mixture of tert-butyl 2-(1-(5-(2-amino-5-chlorophenyl)pyridin-2-yl)-2-phenylethyl)-1-((2-(trimethylsilyl)ethoxy)methyl)-1H-benzo[d]imidazole-5-carboxylate (2-D) (70 mg, 0.107 mmol), sodium azide (21 mg, 0.32 mmol) and trimethoxymethane (34 mg, 0.32 mmol) in acetic acid (1 ml) in a sealed vial was heated 90° C. for 3 hours. The mixture was cooled and solvent was removed in vacuo. The residue was diluted with ethyl acetate, washed with water, brine and dried over $Na_2SO_4$. The solvent was evaporated under reduced pressure. The residue was purified by column chromatography on silica gel, eluting with EtOAc/hexane to give product 2-E. $^1$H NMR (500 MHz, CDCl3) δ: −0.097 (9H, s), 0.80-0.64 (2H, m), 1.61 (9H, s), 3.34-3.19 (2H, m), 3.58 (1H, dd), 3.83 (1H, dd), 4.88 (1H, m), 5.27 (1H, dd), 5.43 (1H, dd), 7.23-7.07 (6H, m), 7.25 (1H, m), 7.37 (1H, m), 7.44 (1H, dd), 7.51 (2H, m), 7.61 91H, m), 7.82 (1H, d), 7.95 (1H, m), 8.06 (1H, s), 8.28 (2H, m), 8.52 (1H, s).

Step 6. 2-(1-(5-(tert-Butoxycarbonyl)-1-((2-(trimethylsilyl)ethoxy)methyl)-1H-benzo[d]imidazol-2-yl)-2-phenylethyl)-5-(5-chloro-2-(1H-tetrazol-1-yl)phenyl)pyridine 1-oxide (2-F)

To a solution of tert-butyl 2-(1-(5-(5-chloro-2-(1H-tetrazol-1-yl)phenyl)pyridin-2-yl)-2-phenylethyl)-1-((2-(trimethylsilyl)ethoxy)methyl)-1H-benzo[d]imidazole-5-carboxylate (2-E) (60 mg, 0.085 mmol) in MeOH (1 ml) was added $H_2O_2$ (0.037 ml, 0.424 mmol, 37%) and methyltrioxorhenium(VII) (10.56 mg, 0.042 mmol). The mixture was stirred at room temperature for 30 minutes. The reaction mixture was washed with $NaHSO_3$ (10% aq.), brine and concentrated to give the crude pyridine N-oxide product 2-F. MS (ESI) m/z 724 (M+H).

Step 7. 2-(1-(5-carboxy-1H-benzo[d]imidazol-2-yl)-2-phenylethyl)-5-(5-chloro-2-(1H-tetrazol-1-yl)phenyl)pyridine 1-oxide (2-G)

A solution of 2-(1-(5-(tert-butoxycarbonyl)-1-((2-(trimethylsilyl)ethoxy)methyl)-1H-benzo[d]imidazol-2-yl)-2-phenylethyl)-5-(5-chloro-2-(1H-tetrazol-1-yl)phenyl)pyridine 1-oxide TFA (1 ml) was added to (2-F) in $CH_2Cl_2$ (1 ml). The solution was heated at 50° C. for 30 minutes. The solvent was removed in vacuo. The residue was purified by reverse phase HPLC, eluting with ACN and water with 0.05% TFA. The product fraction was freeze dried to give the desired product (2-G) (Example 4). MS (ESI) m/z 538 (M+H).

2-(1-(5-carboxy-1H-benzo[d]imidazol-2-yl)-2-phenylethyl)-5-(5-chloro-2-(1H-tetrazol-1-yl)phenyl)pyridine 1-oxide (2-G) was resolved by SFC with a chiral column (AD-H) to give (S)-2-(1-(5-carboxy-1H-benzo[d]imidazol-2-yl)-2-phenylethyl)-5-(5-chloro-2-(1H-tetrazol-1-yl)phenyl)pyridine 1-oxide (Example 5) and (R)-2-(1-(5-carboxy-1H-benzo[d]imidazol-2-yl)-2-phenylethyl)-5-(5-chloro-2-(1H-tetrazol-1-yl)phenyl)pyridine 1-oxide (Example 6). $^1$H NMR (500 MHz, acetone-$d_6$) δ: 3.71-3.57 (2H, m), 5.31 (1H, m), 7.00 (1H, m), 7.14 (1H, m), 7.28-7.19 (4H, m), 7.59 (2H, m), 7.85 (3H, m), 7.92 (1H, m), 8.28 (1H, s) 9.32 (1H, s)

Examples 7, 8 and 9

5-(5-chloro-2-(1H-tetrazol-1-yl)phenyl)-2-(1-(5-fluoro-1H-benzo[d]imidazol-2-yl)-2-phenylethyl) pyridine 1-oxide (Example 7)

(S)-5-(5-chloro-2-(1H-tetrazol-1-yl)phenyl)-2-(1-(5-fluoro-1H-benzo[d]imidazol-2-yl)-2-phenylethyl) pyridine 1-oxide (Example 8) and (R)-5-(5-chloro-2-(1H-tetrazol-1-yl)phenyl)-2-(1-(5-fluoro-1H-benzo[d]imidazol-2-yl)-2-phenylethyl) pyridine 1-oxide (Example 9)

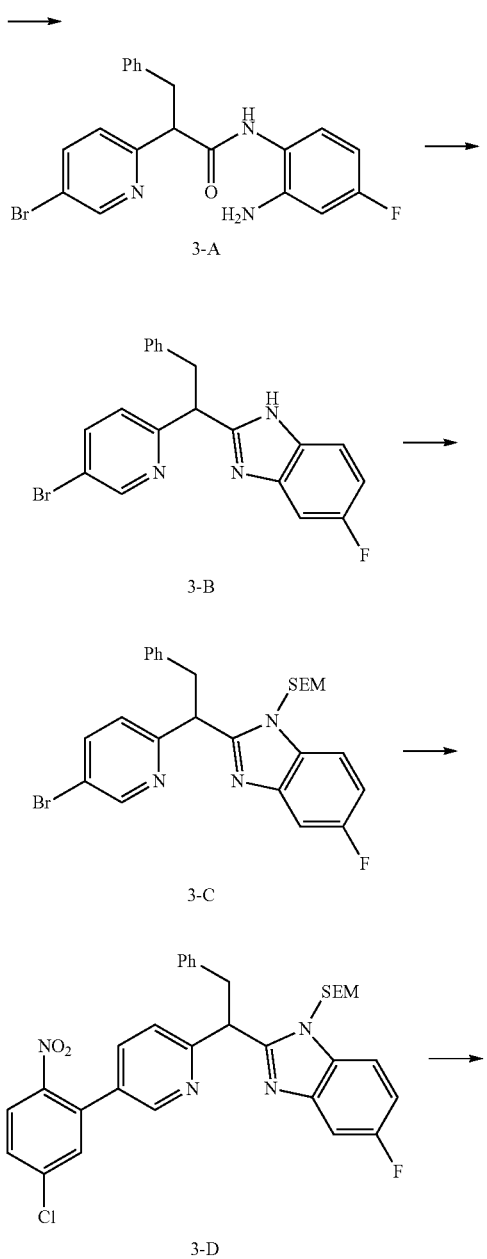

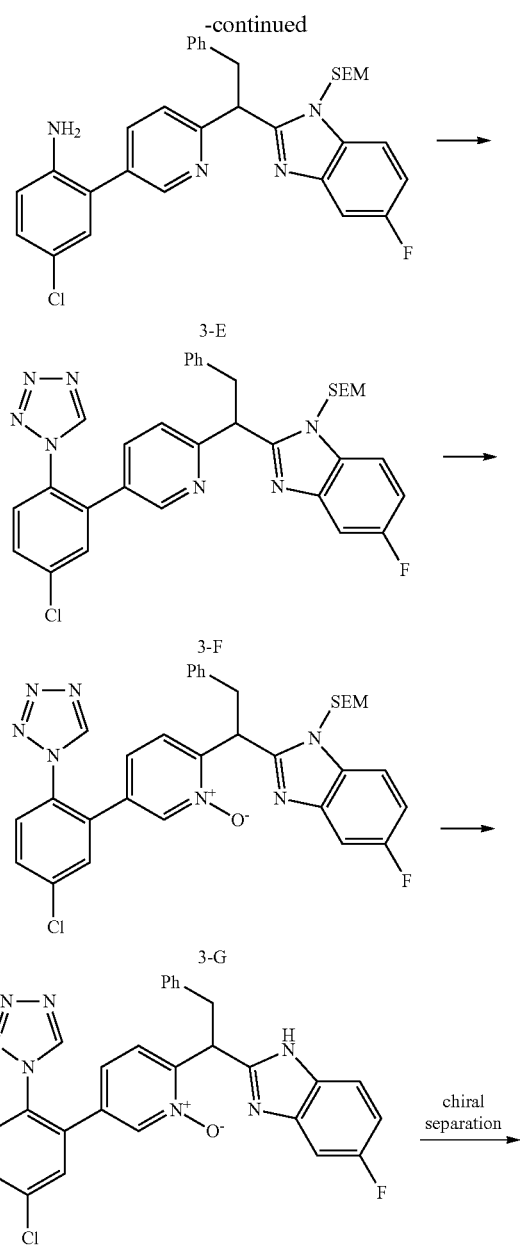

3-H, Example 7

Example 8 (S)
Example 9 (R)

Step 1. N-(2-amino-5-fluorophenyl)-2-(5-bromopyridin-2-yl)-3-phenylpropanamide (3-A)

Compound 3-A was prepared by using the method described in Step 1 of Example 4, 5 and 6. $^1$H NMR (500 MHz, CDCl$_3$) δ: 3.26 (1H, dd), 3.49 (1H, dd), 4.05 (1H, m), 6.40 (2H, d), 6.98 (1H, d), 7.09 (3H m), 7.25-7.17 (3H, m), 7.74 (1H, m), 8.67 (1H, s), 8.73 (1H, s).

Step 2. 2-(1-(5-bromopyridin-2-yl)-2-phenylethyl)-5-fluoro-1H-benzo[d]imidazole (3-B)

A solution of N-(2-amino-5-fluorophenyl)-2-(5-bromopyridin-2-yl)-3-phenylpropanamide (3-A) (1.2 g, 2.9 mmol) in HOAc (15 ml) was heated at 70° C. for 3 hours. The solvent was removed. The residue was partitioned between EtOAc and saturated NaHCO$_3$ (aq). The organic layer was washed with brine, dried (MgSO$_4$), filtered and the solvent was evaporated under reduced pressure to give the crude product 3-B which was used in the next step without purification. MS (ESI) m/z 396 (M+H).

Step 3. 2-(1-(5-Bromopyridin-2-yl)-2-phenylethyl)-5-fluoro-1-((2-(trimethylsilyl)ethoxy)methyl)-1H-benzo[d]imidazole (3-C)

Compound 3-C was prepared by using the method described in Step 3 of Example 4, 5 and 6. $^1$H NMR (500 MHz, CDCl$_3$) δ: -0.097 (9H, s), 0.70 (2H, m), 3.21 (2H, m), 3.55 (1H, dd), 3.82 (1H, dd), 4.80 (1H, m), 5.22 (1H, dd), 5.40 (1H, dd), 7.02 (1H, d), 7.06 (1H, d), 7.20-7.12 (5H m), 7.35 (1H, m), 7.79-7.70 (2H, m), 8.55 (1H, s).

Step 4. 2-(1-(5-(5-chloro-2-nitrophenyl)pyridin-2-yl)-2-phenylethyl)-5-fluoro-1-((2-(trimethylsilyl)ethoxy)methyl)-1H-benzo[d]imidazole) (3-D)

A reaction mixture of 2-(1-(5-Bromopyridin-2-yl)-2-phenylethyl)-5-fluoro-1-((2-(trimethylsilyl)ethoxy)methyl)-1H-benzo[d]imidazole (3-C) (150 mg, 0.28 mmol), PdCl$_2$(dppf) (62.5 mg, 0.085 mmol), (5-chloro-2-nitrophenyl)boronic acid (86 mg, 0.427 mmol) and potassium phosphate tribasic aq. solution (0.57 ml, 1.14 mmol, 2M) in THF (2 ml) was degassed and refilled with N$_2$. It was heated at 100° C. for 1 hour by microwave. The reaction mixture was diluted with water, extracted with EtOAc, the organic was washed with brine, dried over Na$_2$SO$_4$. Solvent was removed in vacuo. The residue was purified by column chromatography on silica gel, eluting with EtOAc/hexane to give the product (3-D). $^1$H NMR (500 MHz, CDCl$_3$) δ: -0.097 (9H, s), 0.79-0.64 (2H, m), 3.30-3.18 (2H, m), 3.62 (1H, m), 3.89 (1H, m), 4.90 (1H, m), 5.27 (1H, dd), 5.45 (1H, dd), 7.03 (1H, m), 7.23-7.12 (6H, m), 7.31 (1H, m), 7.36 (1H, m), 7.60-7.49 (3H, m), 7.79 (1H, m), 7.96 (1H, d,) 8.46 (1H, s).

Step 5. 4-chloro-2-(6-(1-(5-fluoro-1-((2-(trimethylsilyl)ethoxy)methyl)-1H-benzo[d]imidazol-2-yl)-2-phenylethyl)pyridin-3-yl)aniline (3-E)

A reaction mixture of 2-(1-(5-(5-chloro-2-nitrophenyl)pyridin-2-yl)-2-phenylethyl)-5-fluoro-1-((2-(trimethylsilyl)ethoxy)methyl)-1H-benzo[d]imidazole) (3-D) (0.12 g, 0.2 mmol) and tin(II) chloride dihydrate (0.18 g, 0.8 mmol) in EtOH (2 ml) and EtOAc (1 ml) was heated at 50° C. for 3 hours. The reaction mixture was cooled and diluted with EtOAc. It was quenched with 1N NaOH aqueous solution. The product was extracted by EtOAc. The combined organic phase was washed with brine and dried over Na$_2$SO$_4$. The solvent was removed in vacuo to give the desired product 3-E. $^1$H NMR (500 MHz, CDCl$_3$) δ: -0.10 (9H, s), 0.79-0.64 (2H, m), 3.30-3.18 (2H, m), 3.72-3.62 (2H, m), 3.89 (1H, m), 4.92 (1H, dd), 5.27 (1H, dd), 5.50 (1H, dd), 6.70 (1H, d), 7.03 (1H, m), 7.21-7.07 (8H, m), 7.31 (1H, m), 7.55 (1H, m), 7.72 (1H, m), 8.57 (1H, s).

Step 6. 2-(1-(5-(5-Chloro-2-(1H-tetrazol-1-yl)phenyl)pyridin-2-yl)-2-phenylethyl)-5-fluoro-1((2-(trimethylsilyl)ethoxy)methyl)-1H-benzo[d]imidazole (3-F)

Compound 3-F was prepared by using the method described in Step 5 of Example 4, 5 and 6. $^1$H NMR (500 MHz, CDCl$_3$) δ: −0.090 (9H, s), 0.81-0.65 (2H, m), 3.30-3.19 (2H, m), 3.55 (1H, dd), 3.82 (1H, dd), 4.83 (1H, m), 5.22 (1H, dd), 5.40 (1H, dd), 7.07-7.00 (2H, m), 7.11 (1H, d), 7.30-7.15 (5H m), 7.35 (1H, m), 7.52 (2H, m), 7.60 (1H, m), 7.75 (1H, m), 8.28 (2H, m).

Step 7. 5-(5-Chloro-2-(1H-tetrazol-1-yl)phenyl)-2-(1-(5-fluoro-1-((2-(trimethylsilyl)ethoxy)methyl)-1H-benzo[d]imidazol-2-yl)-2-phenylethyl)pyridine 1-oxide (3-G)

Compound 3-G was prepared by using the method described in Step 6 of Example 4, 5 and 6. MS (ESI) m/z 642 (M+H).

Step 8. 5-(5-chloro-2-(1H-tetrazol-1-yl)phenyl)-2-(1-(5-fluoro-1H-benzo[d]imidazol-2-yl)-2-phenylethyl)pyridine 1-oxide (3-H, Example 7)

Compound 3-H was prepared by using the method described in Step 7 of Example 4, 5 and 6. MS (ESI) m/z 512 (M+H). 5-(5-chloro-2-(1H-tetrazol-1-yl)phenyl)-2-(1-(5-fluoro-1H-benzo[d]imidazol-2-yl)-2-phenylethyl)pyridine 1-oxide (Example 7) was resolved by SFC with a chiral column (Whelk-O®1) to give (S)-5-(5-chloro-2-(1H-tetrazol-1-yl)phenyl)-2-(1-(5-fluoro-1H-benzo[d]imidazol-2-yl)-2-phenylethyl)pyridine 1-oxide (Example 8) and (R)-5-(5-chloro-2-(1H-tetrazol-1-yl)phenyl)-2-(1-(5-fluoro-1H-benzo[d]imidazol-2-yl)-2-phenylethyl)pyridine 1-oxide (Example 9). $^1$H NMR (500 MHz, acetone-d$_6$) δ: 3.74 (1H, m), 3.84 (1H, m), 5.62 (1H, m), 7.09 (2H, m), 7.27-7.14 (6H, m), 7.39 (1H, m), 7.54 (2H, m), 7.73-7.65 (3H, m), 8.19 (1H, s) 8.70 (1H, s). By using the procedures described above, and appropriate starting materials, the following compounds were synthesized. These compounds were characterized by LC/MS.

| Ex | Structure | Chiral separation | LCMS [M + H]+ | F11a IC50 (nM) | PK IC50 (nM) |
|---|---|---|---|---|---|
| 1 | 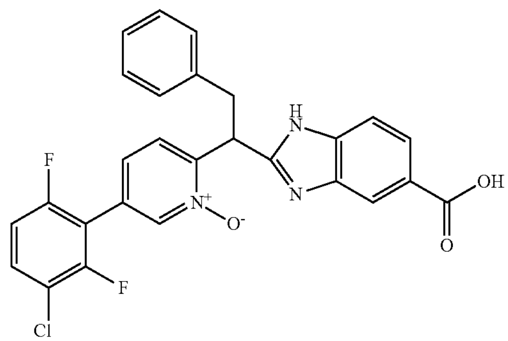 [SMILES: O=C(O)c1ccc2[nH]c(C(Cc3ccccc3)c3ccc(-c4c(F)ccc(Cl)c4F)c[n+]3[O-])nc2c1] | racemic | 506 | 89.20 | 293.00 |
| 2 | 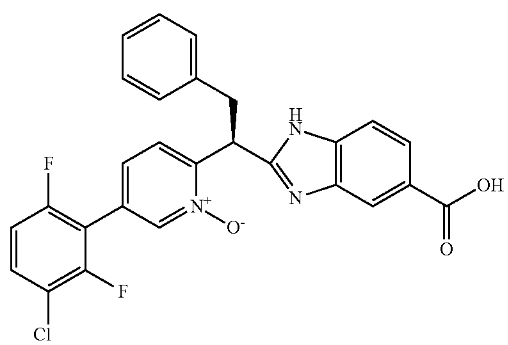 [SMILES: O=C(O)c1ccc2[nH]c([C@H](Cc3ccccc3)c3ccc(-c4c(F)ccc(Cl)c4F)c[n+]3[O-])nc2c1] | Fast eluting isomer on OD-H chiral column | 506 | 46.2 | 182 |
| 3 | 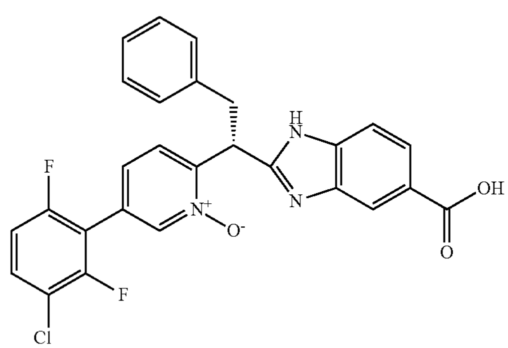 [SMILES: O=C(O)c1ccc2[nH]c([C@@H](Cc3ccccc3)c3ccc(-c4c(F)ccc(Cl)c4F)c[n+]3[O-])nc2c1] | Slow eluting isomer on OD-H chiral column | 506 | 138 | 181.90 |

-continued

| Ex | Structure | Chiral separation | LCMS [M + H]+ | F11a IC50 (nM) | PK IC50 (nM) |
|---|---|---|---|---|---|
| 4 | 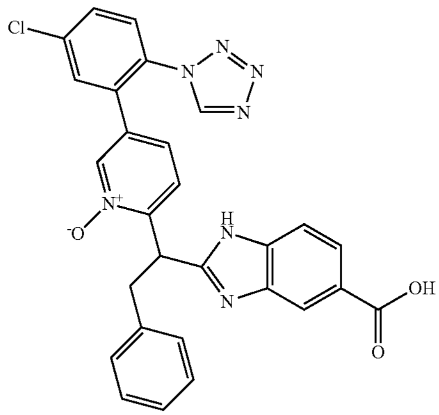 | racemic | 538 | 0.45 | 52.71 |
| 5 | 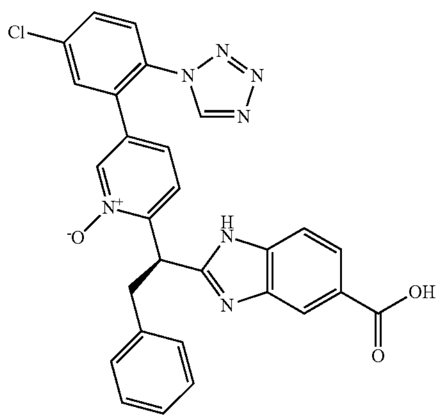 | Eanotiomer 1 Chiral AD-H column | 538 | 3.41 | 216.00 |
| 6 | 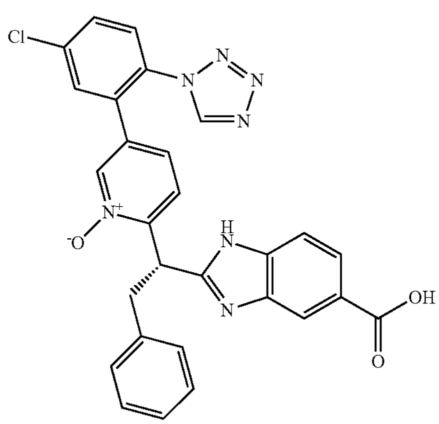 | Eanotiomer 2 Chiral AD-H column | 538 | 0.51 | 28.35 |

-continued

| Ex | Structure | Chiral separation | LCMS [M + H]+ | F11a IC50 (nM) | PK IC50 (nM) |
|----|-----------|-------------------|---------------|----------------|--------------|
| 7 | 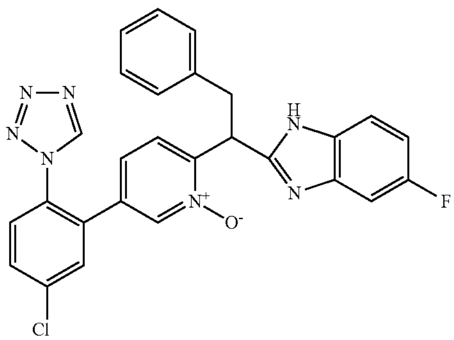 | racemic | 512 | 1.15 | 185.60 |
| 8 | 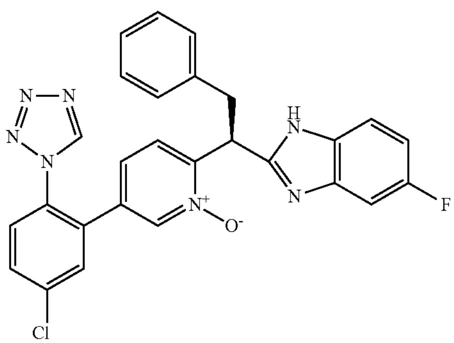 [SMILES: [O-][n+]1cc(-c2cc(Cl)ccc2-n2cnnn2)ccc1[C@@H](Cc1ccccc1)c1nc2cc(F)ccc2[nH]1] | Enantiomer 1 Chrial Whelk-O1 column | 512 | 1.33 | 123.70 |
| 9 | 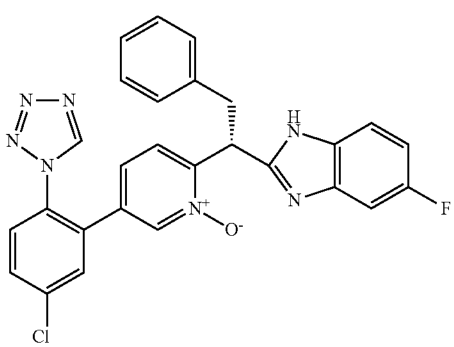 [SMILES: [O-][n+]1cc(-c2cc(Cl)ccc2-n2cnnn2)ccc1[C@H](Cc1ccccc1)c1nc2cc(F)ccc2[nH]1] | Enantiomer 2 Chrial Whelk-O1 column | 512 | 3.28 | 295.00 |
| 10 | 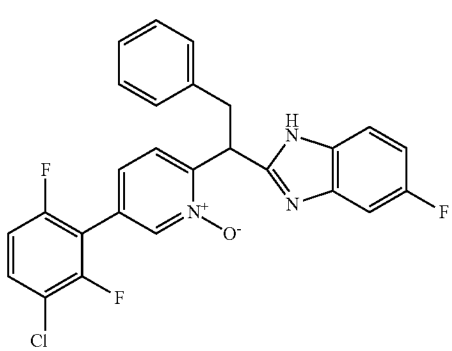 [SMILES: [O-][n+]1cc(-c2c(F)ccc(Cl)c2F)ccc1C(Cc1ccccc1)c1nc2cc(F)ccc2[nH]1] | racemic | 480 | 1246.00 | |

-continued

| Ex | Structure | Chiral separation | LCMS [M + H]+ | F11a IC50 (nM) | PK IC50 (nM) |
|---|---|---|---|---|---|
| 11 | 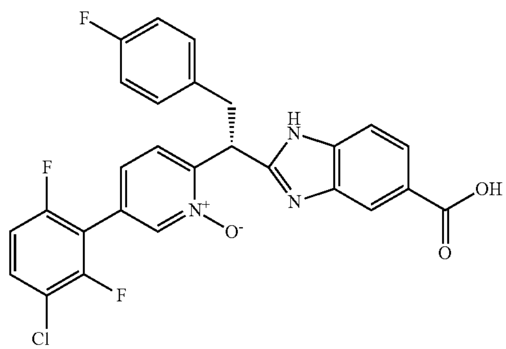 [SMILES: O=C(O)c1ccc2[nH]c([C@@H](Cc3ccc(F)cc3)c3ccc(-c4c(F)ccc(Cl)c4F)c[n+]3[O-])nc2c1] | Fast eluting isomer OD-H column | 524 | 145.90 | |
| 12 | 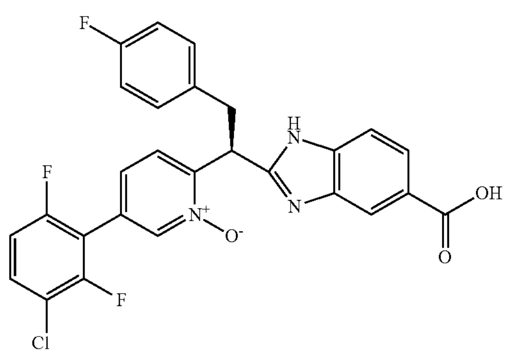 [SMILES: O=C(O)c1ccc2[nH]c([C@H](Cc3ccc(F)cc3)c3ccc(-c4c(F)ccc(Cl)c4F)c[n+]3[O-])nc2c1] | Slow eluting isomer OD-H column | 524 | 160.20 | |
| 13 | 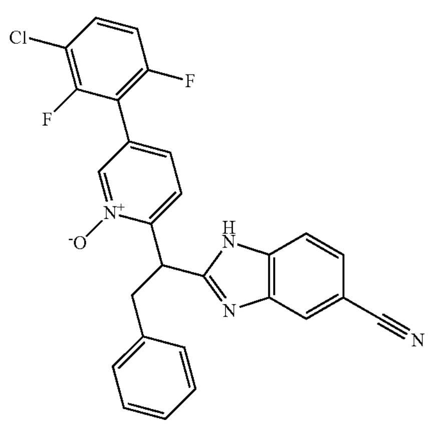 | racemic | 487 | 1876.00 | |
| 14 | 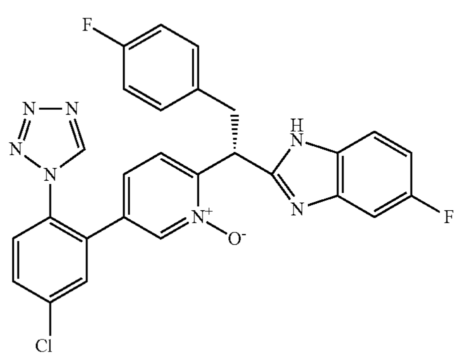 [SMILES: [O-][n+]1cc(-c2cc(Cl)ccc2-n2cnnn2)ccc1[C@H](Cc1ccc(F)cc1)c1nc2cc(F)ccc2[nH]1] | Fast eluting isomer Chiral Whelk O1 column | 530 | 89.70 | 809.00 |

-continued
| Ex | Structure | Chiral separation | LCMS [M + H]+ | F11a IC50 (nM) | PK IC50 (nM) |
|---|---|---|---|---|---|
| 15 | 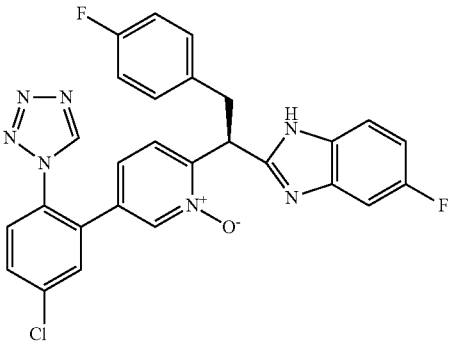 [SMILES: [O-][n+]1cc(-c2cc(Cl)ccc2-n2cnnn2)ccc1[C@@H](Cc1ccc(F)cc1)c1nc2cc(F)ccc2[nH]1] | Slow eluting isomer Chiral Whelk O1 column | 530 | 4.70 | 244.80 |
| 16 | 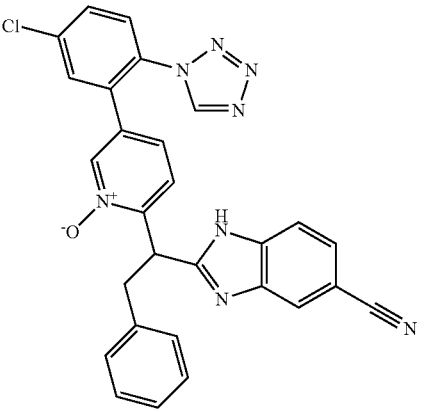 | racemic | 519 | 1.33 | 150.50 |
| 17 | 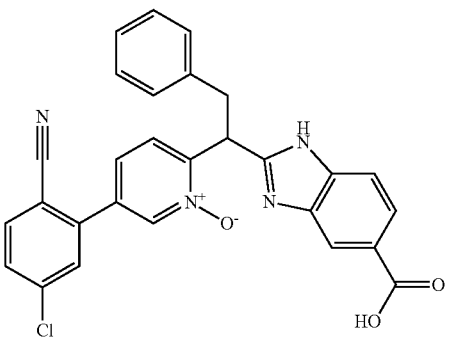 [SMILES: N#Cc1ccc(Cl)cc1-c1ccc(C(Cc2ccccc2)c2nc3cc(C(=O)O)ccc3[nH]2)[n+]([O-])c1] | racemic | 495 | 38.19 | 335.30 |
| 18 | 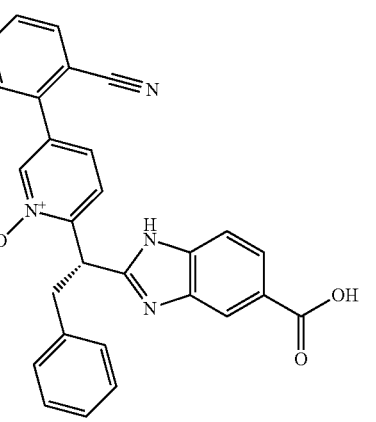 | Fast eluting isomer Chrial AD-H column | 495 | 25.41 | 105.60 |

| Ex | Structure | Chiral separation | LCMS [M + H]+ | F11a IC50 (nM) | PK IC50 (nM) |
|---|---|---|---|---|---|
| 19 | 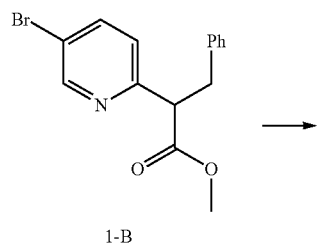 | Slow eluting isomer Chrial AD-H column | 495 | 27.86 | 174.40 |
Examples 20 and 21
2-[(1R)-1-{5-[3-chloro-2-fluoro-6-(1H-tetrazol-1-yl)phenyl]-1-oxidopyridin-2-yl}-2-phenylethyl]-5-fluoro-1H-benzimidazole (Example 20)
2-[(1S)-1-{5-[3-chloro-2-fluoro-6-(1H-tetrazol-1-yl)phenyl]-1-oxidopyridin-2-yl}-2-phenylethyl]-5-fluoro-1H-benzimidazole (Example 21)
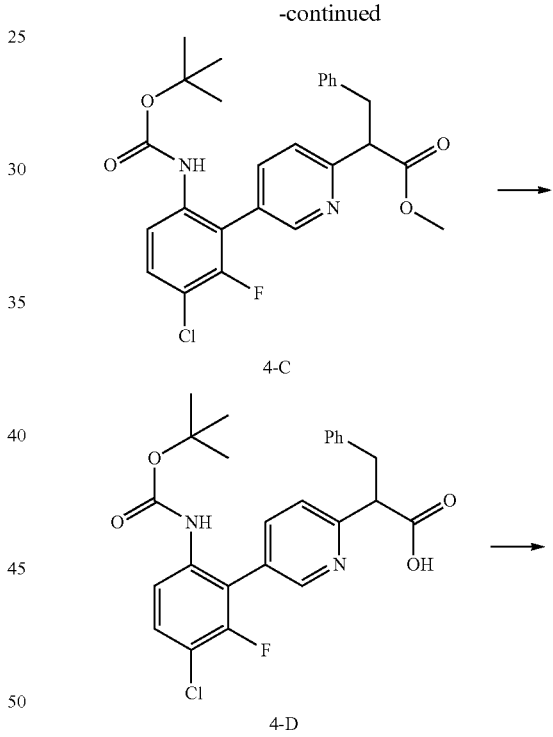
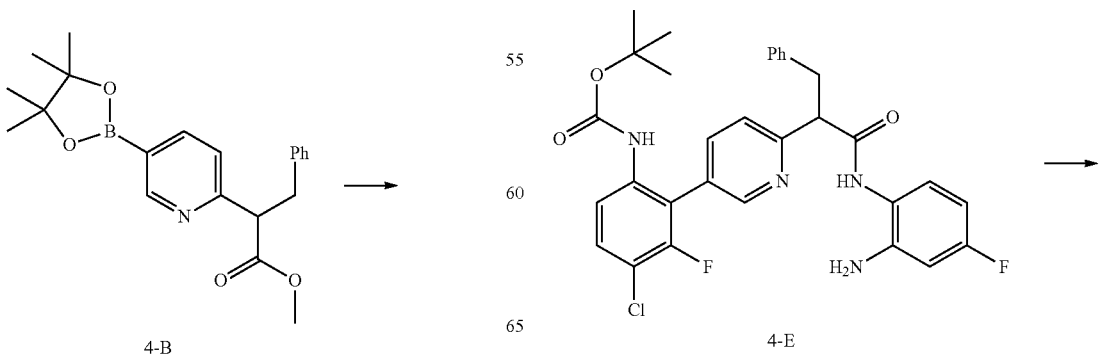

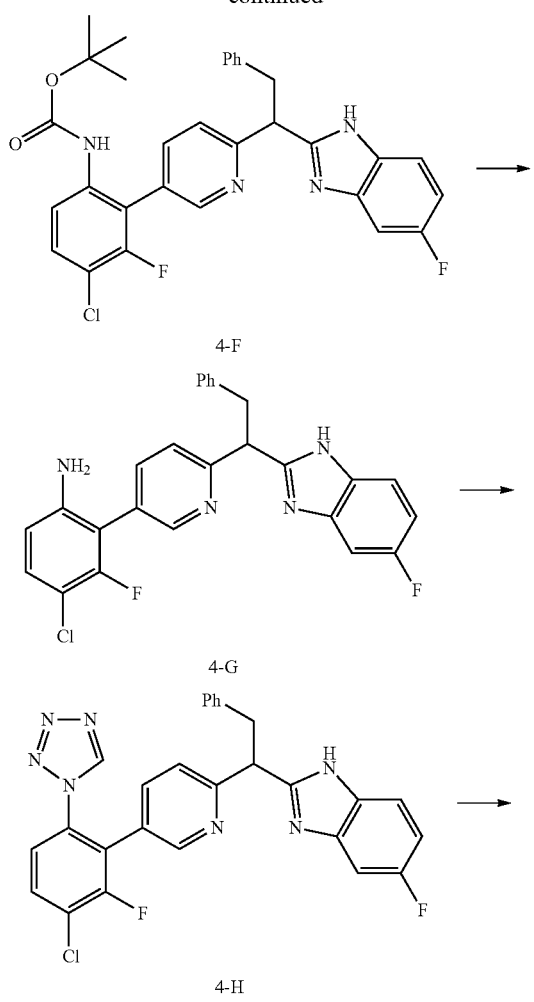

4-F

4-G

4-H

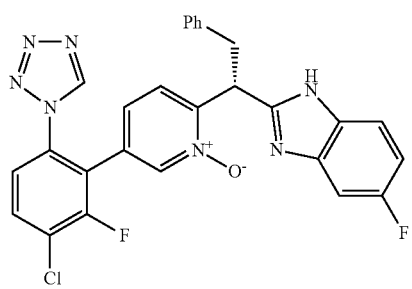

Example 20

Example 21

Step 1. Methyl 3-phenyl-2-(5-(4,4,5,5-tetramethyl-1,3,2-dioxaborolan-2-yl)pyridin-2-yl)propanoate (4-B)

Bis(pinacolato)diboron (0.51 g, 2.0 mmol) was mixed with [1,1'-bis(diphenylphosphino)ferrocene]dichloropalladium(II) (0.37 g, 0.50 mmol) and potassium acetate (0.59 g, 6.0 mmol) in a microwave reaction vial. The vial was capped. Air was removed and back-filled with nitrogen (×3). 1-B (0.64 g, 2 mmol) in 1,4-Dioxane (9 ml) was then introduced with syringe. Air was removed, and back-filled with nitrogen (×3). The mixture was stirred at 120° C. for 1 hours and was used in the next step directly.

Step 2. Methyl 2-(5-(6-((tert-butoxycarbonyl)amino)-3-chloro-2-fluorophenyl)pyridin-2-yl)-3-phenylpropanoate (4-C)

The reaction mixture from step 1 was mixed with tert-butyl (4-chloro-3-fluoro-2-iodophenyl)carbamate (743 mg, 2.000 mmol) and [1,1'-bis(diphenylphosphino) ferrocene]dichloropalladium(II) (146 mg, 0.20 mmol) in a microwave reaction vial. Potassium carbonate (1M, 6.0 ml) was added. The vial was then capped. Air was removed by vacuum and back-filled with nitrogen (×3). The mixture was then heated to 80° C. for 1 hour. The mixture was diluted with ethyl acetate, and partitioned with brine. The mixture was filtered. The organic layer was separated, and dried over anhydrous sodium sulfate. After it was filtered and concentrated, the crude was purified by column chromatography on a 50 g prepacked silica gel column, eluting with gradient 0~50% EtOAc/hexane to give 4-C. MS (ESI) m/z 485 (M+H).

Step 3. 2-(5-(6-((tert-butoxycarbonyl)amino)-3-chloro-2-fluorophenyl)pyridin-2-yl)-3-phenylpropanoic acid (4-D)

4-C (270 mg, 0.56 mmol) in MeOH (1.8 ml) was mixed with LiOH (1M, 0.84 ml). The mixture was stirred for 1 hour at 50° C. The mixture was then concentrated, and further dried in vacuum oven at 50° C. overnight. The lithium salt of 4-D was used in the next step without further purification. MS (ESI) m/z 471 (M+H).

Step 4. tert-Butyl (2-(6-(1-((2-amino-5-fluorophenyl)amino)-1-oxo-3-phenylpropan-2-yl)pyridin-3-yl)-4-chloro-3-fluorophenyl)carbamate (4-E)

The lithium salt of 4-D (235 mg, 0.5 mmol) in DMF (2.0 ml) was mixed with 4-fluorobenzene-1,2-diamine (76 mg, 0.60 mmol) and HATU (209 mg, 0.55 mmol). The mixture was stirred for 2 hour at 50° C., then poured into 70 mL of water. The precipitate was collected by filtration, and washed with water, then dried in vacuum oven vacuum oven at 50° C. overnight to give 4-E. MS (ESI) m/z 579 (M+H).

Step 5. tert-Butyl (4-chloro-3-fluoro-2-(6-(1-(5-fluoro-1H-benzo[d]imidazol-2-yl)-2-phenylethyl)pyridin-3-yl)phenyl)carbamate (4-F)

4-E (0.26 g, 0.45 mmol) in acetic acid (5 ml) were heated to 95° C. for 3 hours. The mixture was concentrated. The residue was taken up with ethyl acetate, then washed with saturated sodium bicarbonate solution and brine. The organic layer was separated, and dried over anhydrous sodium sulfate. After it was filtered, the solution was concentrated, and purified by column chromatography on a 50 g prepacked silica gel column, and eluting with 0~70% gradient EtOAc/hexane to give 4-F. MS (ESI) m/z 561 (M+H).

Step 6. 4-Chloro-3-fluoro-2-(6-(1-(5-fluoro-1H-benzo[d]imidazol-2-yl)-2-phenylethyl)pyridin-3-yl)aniline (4-G)

(4-F): (220 mg, 0.39 mmol) was treated with 4M HCl in dioxane at room temperature for 30 minutes. The mixture was concentrated and further dried in vacuum oven at 50° C. overnight to give 4-G. MS (ESI) m/z 461 (M+H).

Step 7. 2-(1-(5-(3-chloro-2-fluoro-6-(1H-tetrazol-1-yl)phenyl)pyridin-2-yl)-2-phenylethyl)-5-fluoro-1H-benzo[d]imidazole (4-H)

4-G (170 mg, 0.37 mmol) was mixed with trimethyl orthoformate (0.41 ml, 3.7 mmol) and sodium azide (240 mg, 3.7 mmol). The vial was capped. Acetic acid (4 ml) was then added with syringe. The mixture was stirred at room temperature overnight, then concentrated. The residue was diluted with ethyl acetae, and washed with diluted sodium bicarbonate solution and brine. After it was dried over anhydrous sodium sulfate, the solution was filtered, and concentrated. The crude was purified by column chromatography on a 50 g prepacked silica gel column, eluting with gradient 10~100% EtOAc/isohexane to give 4-H. MS (ESI) m/z 514 (M+H).

Step 8. 2-[(1R)-1-{5-[3-chloro-2-fluoro-6-(1H-tetrazol-1-yl)phenyl]-1-oxidopyridin-2-yl}-2-phenylethyl]-5-fluoro-1H-benzimidazole (Example 20), and 2-[(1S)-1-{5-[3-chloro-2-fluoro-6-(1H-tetrazol-1-yl)phenyl]-1-oxidopyridin-2-yl}-2-phenylethyl]-5-fluoro-1H-benzimidazole (Example 21)

4-H (150 mg, 0.29 mmol) in acetic acid (1.5 ml) was mixed with peracetic acid (0.49 ml, 2.9 mmol) and TFA (0.10 ml). The mixture was stirred at room temperature overnight. Toluene was added to the mixture. The solvent was evaporated by rotavapor. The residue was taken up with ethyl acetate, and washed with saturated aq. sodium bicarbonate solution, and brine. The organic layer was separated, and dried over anhydrous sodium sulfate. The solution was filtered, and concentrated, then purified by column chromatography on a 50 g prepacked silica gel column, eluting with gradient 20~100% EtOAc/isohexane to give the racemic product. Chiral separation of the racemic mixture on an OD-H column, eluting with 45% MeOH/CO2, to give Example 20 (fast eluting isomer, MS (ESI) m/z 530 (M+H), and Example 21 (slow eluting isomer, MS (ESI) m/z 530 (M+H).

Examples 22 and 23

(R)-5-(2-carbamoyl-5-chlorophenyl)-2-(1-(5-fluoro-1H-benzo[d]imidazol-2-yl)-2-phenylethyl)pyridine 1-oxide (Example 22), and (S)-5-(2-carbamoyl-5-chlorophenyl)-2-(1-(5-fluoro-1H-benzo[d]imidazol-2-yl)-2-phenylethyl)pyridine 1-oxide (Example 23)

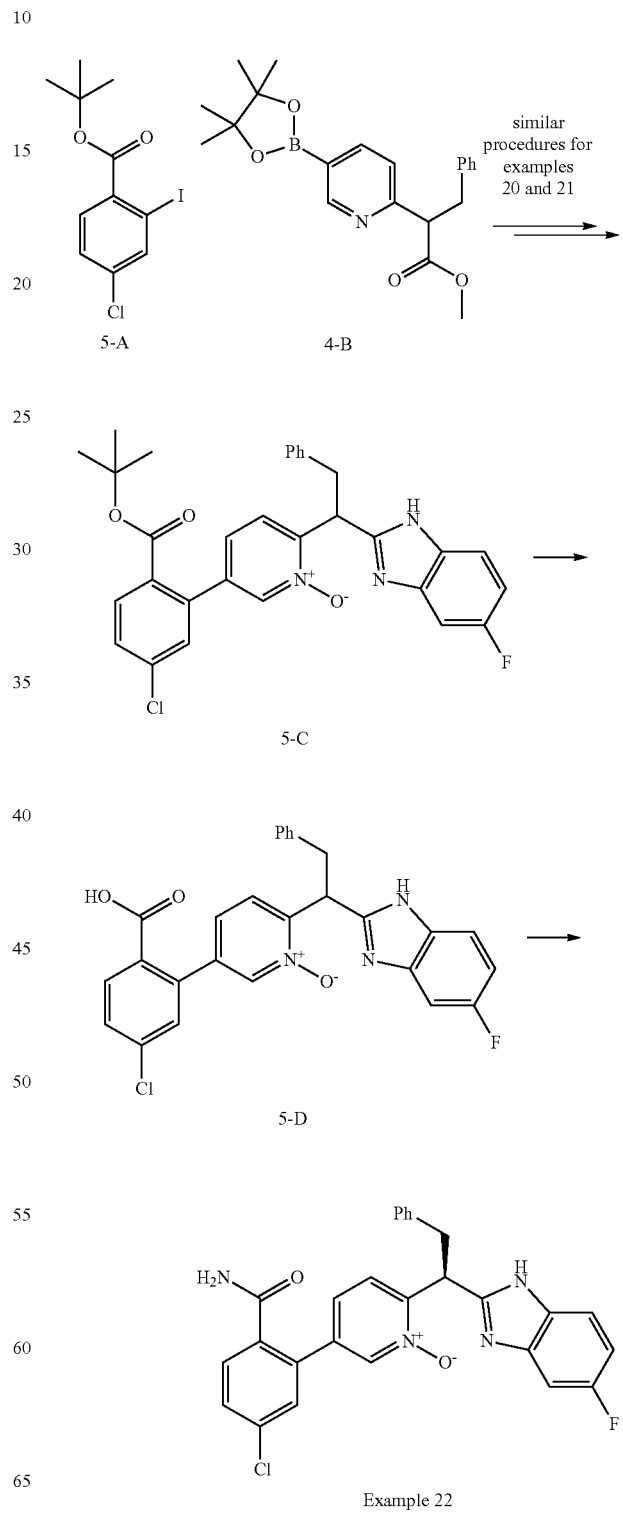

Example 22

49

-continued

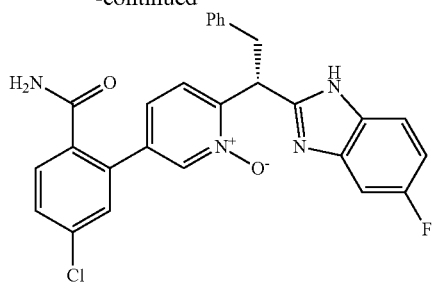

Example 23

Step 1. 5-(2-(tert-butoxycarbonyl)-5-chlorophenyl)-2-(1-(5-fluoro-1H-benzo[d]imidazol-2-yl)-2-phenylethyl)pyridine 1-oxide (5-C)

Beginning with tert-Butyl 4-chloro-2-iodobenzoate and 4-B, intermediate 5-C was obtained using similar procedures (steps 2-5 and the N-oxidation procedure in step 8) for Examples 20 and 21. MS (ESI) m/z 544 (M+H).

Step 2. 5-(2-carboxy-5-chlorophenyl)-2-(1-(5-fluoro-1H-benzo[d]imidazol-2-yl)-2-phenylethyl)pyridine 1-oxide (5-D)

5-C (450 mg, 0.83 mmol) was stirred in a mixed solvent of TFA (3 ml) and DCM (3.00 ml) at room temperature for 2 hours. The mixture was then concentrated, co-evaporated twice with toluene, then further dried in vacuum oven at 50° C. overnight. The product was used in the next step without further purification. MS (ESI) m/z 488 (M+H).

Step 3. (R)-5-(2-carbamoyl-5-chlorophenyl)-2-(1-(5-fluoro-1H-benzo[d]imidazol-2-yl)-2-phenylethyl)pyridine 1-oxide (Example 22), and (S)-5-(2-carbamoyl-5-chlorophenyl)-2-(1-(5-fluoro-1H-benzo[d]imidazol-2-yl)-2-phenylethyl)pyridine 1-oxide (Example 23)

HATU (47 mg, 0.12 mmol) in DMF (1 ml) was mixed with Hunig's base (0.054 ml, 0.307 mmol) and 5-D (50 mg, 0.102 mmol). The mixture was stirred at room temperature for 15 minutes. Ammonium hydroxide (0.043 ml, 0.307 mmol) was added. After 30 minutes, the mixture was diluted with 2 mL of DMF. The solution was filtered, then purified by preparative HPLC (C-18), eluting with acetonitrile/water+0.1% TFA, to give the racemic product, which was subjected to chiral separation with OJ chiral column, eluting with 18% MeOH/CO2, to give Example 22 (fast eluting isomer, MS (ESI) m/z 487 (M+H), and Example 23 (slow eluting isomer, MS (ESI) m/z 487 (M+H).

50

Examples 24

2-(1-(5-carboxy-1H-benzo[d]imidazol-2-yl)-2-cyclopropylethyl)-5-(5-chloro-2-(1H-tetrazol-1-yl)phenyl)pyridine 1-oxide (Example 24)

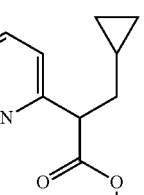

6-A

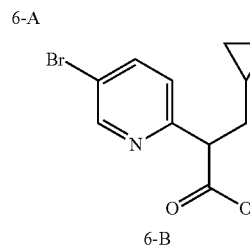

6-B

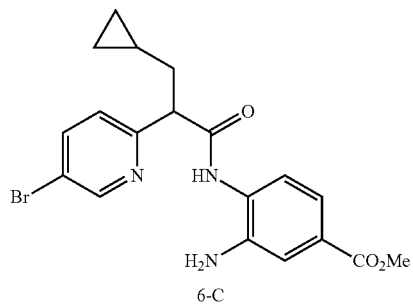

6-C

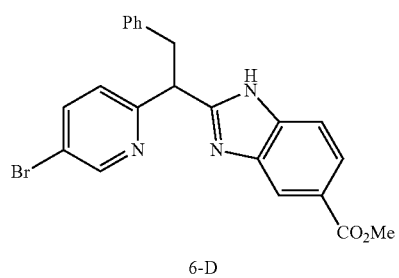

6-D

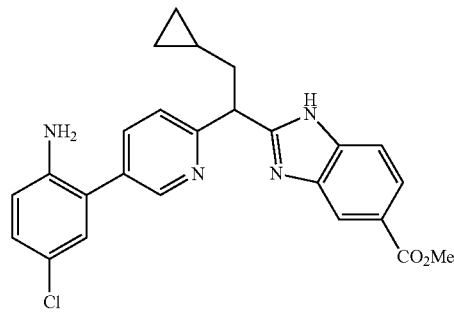

6-E

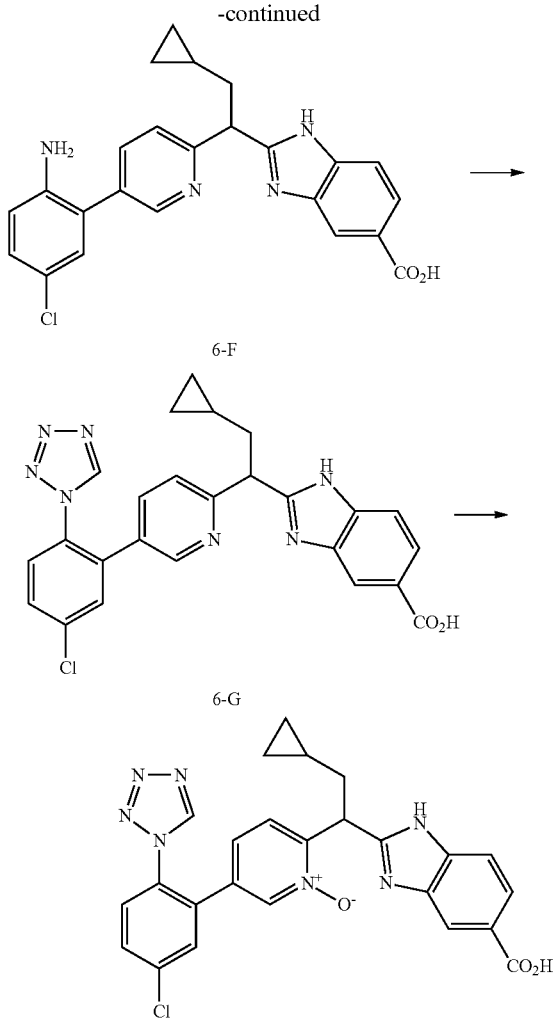

Example 24

Step 1. 2-(5-bromopyridin-2-yl)-3-cyclopropylpropanoic acid (6-B)

Methyl 2-(5-bromopyridin-2-yl)-3-cyclopropylpropanoate (6-A, 1.7 g, 6.0 mmol) in MeOH (19 ml) was mixed with LiOH (8.55 ml, 8.55 mmol) and heated to 50° C. for 30 minutes. The mixture was concentrated to dryness, then further dried in vacuum oven at 50° C. overnight. The product was used directly in the next step without further treatment. MS (ESI) m/z 272 (M+H),

Step 2. Methyl 3-amino-4-(2-(5-bromopyridin-2-yl)-3-cyclopropylpropanamido)benzoate (6-C)

The lithium salt of 6-B (1.7 g, 6.0 mmol) in DMF (12 ml) was mixed with HATU (2.58 g, 6.77 mmol), and methyl 3,4-diaminobenzoate (1.2 g, 7.3 mmol). The mixture was stirred at room temperature for 4 hours. The mixture was poured into 100 mL of water while stirring. The precipitate was collected by filtration, and washed with water. The product was dried in a vacuum oven at 50° C. for 3 days, to afford 6-C. MS (ESI) m/z 418 (M+H).

Step 3. Methyl 2-(1-(5-bromopyridin-2-yl)-2-cyclopropylethyl)-1H-benzo[d]imidazole-5-carboxylate (6-D)

6-C (1 g, 2.391 mmol) in acetic acid (6 ml) was heated to 80° C. overnight. The reaction mixture was concentrated, and the crude was taken up with ethyl acetate (150 mL) and washed with saturated sodium bicarbonate solution, and brine. The organic layer was separated, and dried over anhydrous sodium sulfate. After it was filtered and concentrated, the crude was purified by column chromatography on an 100 g prepacked silica gel column, eluting with gradient 0~5% $CH_2Cl_2$/MeOH to give 6-D. MS (ESI) m/z 401 (M+H).

Step 4. Methyl 2-(1-(5-(2-amino-5-chlorophenyl)pyridin-2-yl)-2-cyclopropylethyl)-1H-benzo[d]imidazole-5-carboxylate (6-E)

6-D (200 mg, 0.5 mmol) was mixed with 4-chloro-2-(4,4,5,5-tetramethyl-1,3,2-dioxaborolan-2-yl)aniline (152 mg, 0.6 mmol), 1,1'-bis(di-tert-butylphosphino)ferrocene palladium dichloride (65 mg, 0.1 mmol), and potassium phosphate tribasic (265 mg, 1.25 mmol) in a microwave reaction vial. The vial was capped, air was removed and back-filled with nitrogen (×3). THF (2 ml) and water (0.5 ml) were then introduced with syringe. Air was removed and back-filled with nitrogen (×3) again. The mixture was then heated to 65° C. for 1 hour. After it was cooled to room temperature, the mixture was diluted with ethyl acetate. The organic layer was separated and concentrated. The crude was purified by column chromatography on a 50 g prepacked silica gel column, eluting with 0~80% gradient EtOAc/hexane to give 6-E. MS (ESI) m/z 447 (M+H).

Step 5. 2-(1-(5-(2-amino-5-chlorophenyl)pyridin-2-yl)-2-cyclopropylethyl)-1H-benzo[d]imidazole-5-carboxylic acid (6-F)

6-E (150 mg, 0.336 mmol) was mixed with LiOH (0.67 ml, 0.67 mmol) in a MeOH (1.3 ml). The mixture was then heated to 50° C. overnight. The mixture was then concentrated to dryness to give 6-F as a lithium salt, and used in the next step without further purification. MS (ESI) m/z 433 (M+H).

Step 6. 2-(1-(5-(5-chloro-2-(1H-tetrazol-1-yl)phenyl)pyridin-2-yl)-2-cyclopropyl ethyl)-1H-benzo[d]imidazole-5-carboxylic acid (6-G)

6-F (143 mg, 0.33 mmol) was mixed with trimethyl orthoformate (0.36 ml, 3.3 mmol) and sodium azide (215 mg, 3.30 mmol) in acetic acid (2 ml). The mixture was then stirred at room temperature overnight. The mixture was concentrated. The crude was purified by column chromatography on a 50 g prepacked silica gel column, eluting with gradient 0~7% $CH_2Cl_2$/MeOH+0.4% acetic acid to give 6-G. MS (ESI) m/z 486 (M+H).

Step 7. 2-(1-(5-carboxy-1H-benzo[d]imidazol-2-yl)-2-cyclopropylethyl)-5-(5-chloro-2-(1H-tetrazol-1-yl)phenyl)pyridine 1-oxide (Example 24)

6-G (107 mg, 0.22 mmol) in acetic acid (1.5 ml) was mixed with peracetic acid (0.36 ml, 1.76 mmol). The mixture was then stirred at room temperature overnight. The mixture was concentrated, and the crude was purified by column chromatography on a 50 g prepacked silica gel column, eluting with gradient 0~8% CH$_2$Cl$_2$/MeOH+0.4% acetic acid to give Example 24. MS (ESI) m/z 502 (M+H).

By using the procedures described above, and using appropriate starting materials, the following compounds were synthesized. These compounds were characterized by LC/MS.

| Ex | Structure | Chiral separation | LCMS [M + H]+ | F11a IC50 (nM) | PK IC50 (nM) |
|---|---|---|---|---|---|
| 20 | 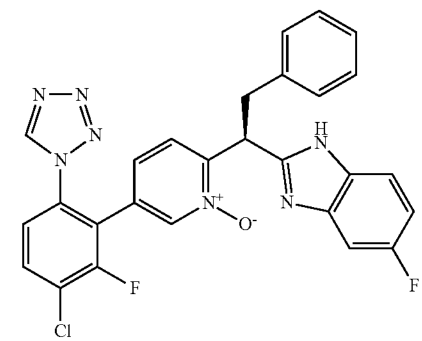 [SMILES: [O-][n+]1cc(-c2c(-n3cnnn3)ccc(Cl)c2F)ccc1[C@@H](Cc1ccccc1)c1nc2cc(F)ccc2[nH]1] | Fast eluting isomer on chiral OD column, 45% MeOH/CO2 | 530 | 1.82 | 64.84 |
| 21 | 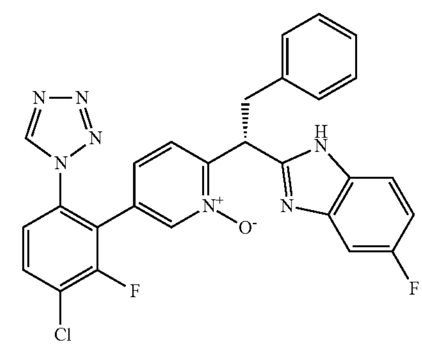 [SMILES: [O-][n+]1cc(-c2c(-n3cnnn3)ccc(Cl)c2F)ccc1[C@H](Cc1ccccc1)c1nc2cc(F)ccc2[nH]1] | slow eluting isomer on chiral OD column, 45% MeOH/CO2 | 530 | 11.79 | 169.40 |
| 22 | 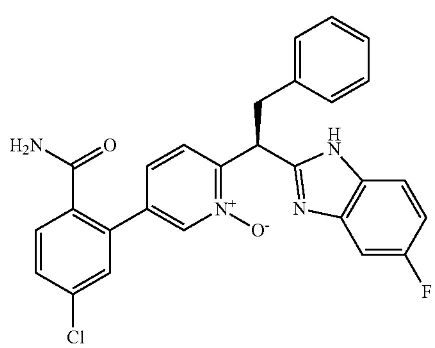 [SMILES: NC(=O)c1ccc(Cl)cc1-c1ccc([C@@H](Cc2ccccc2)c2nc3cc(F)ccc3[nH]2)[n+]([O-])c1] | Fast eluting isomer on OJ chiral column, 18% MeOH/CO2 | 487 | 154.50 | |
| 23 | 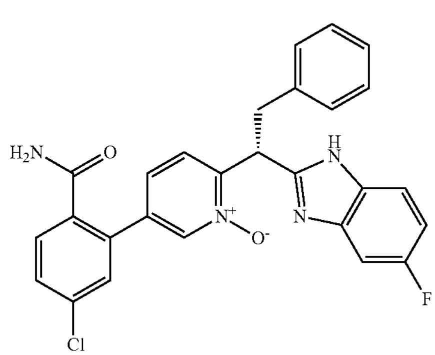 [SMILES: NC(=O)c1ccc(Cl)cc1-c1ccc([C@H](Cc2ccccc2)c2nc3cc(F)ccc3[nH]2)[n+]([O-])c1] | Slow eluting isomer on OJ chiral column, 18% MeOH/CO2 | 487 | 1000.00 | |

| Ex | Structure | Chiral separation | LCMS [M + H]+ | F11a IC50 (nM) | PK IC50 (nM) |
|---|---|---|---|---|---|
| 24 | 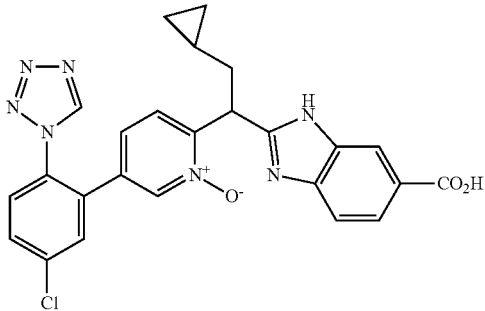 [SMILES: O=C(O)c1ccc2nc(C(CC3CC3)c3ccc(-c4cc(Cl)ccc4-n4cnnn4)c[n+]3[O-])[nH]c2c1] | racemic | 502 | 14.2 | |
| 25 | 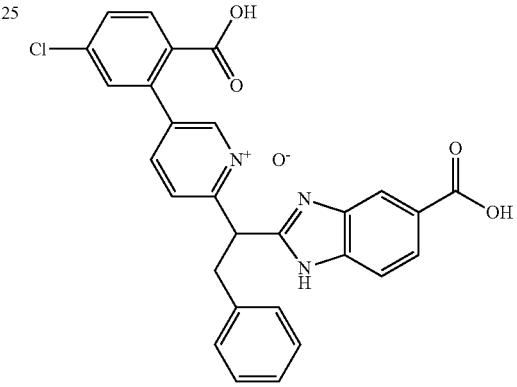 | racemic | 514 | 54.04 | 2735.00 |
| 26 | 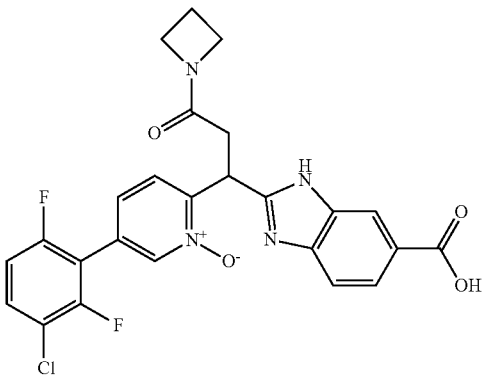 [SMILES: O=C(O)c1ccc2nc(C(CC(=O)N3CCC3)c3ccc(-c4c(F)ccc(Cl)c4F)c[n+]3[O-])[nH]c2c1] | racemic | 513 | 7929.00 | |
| 27 | 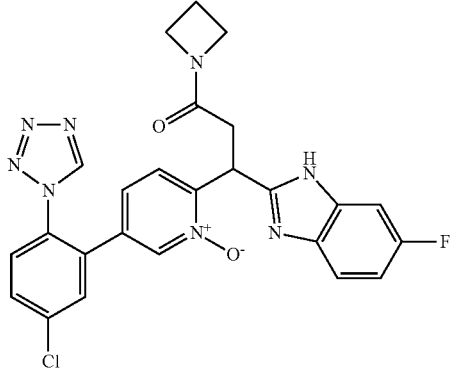 [SMILES: O=C(CC(c1nc2ccc(F)cc2[nH]1)c1ccc(-c2cc(Cl)ccc2-n2cnnn2)c[n+]1[O-])N1CCC1] | Fast eluting isomer, chiral IA column, 70% 2:1 MeOH:MeCN/CO2 | 519 | 79.12 | |

| Ex | Structure | Chiral separation | LCMS [M + H]+ | F11a IC50 (nM) | PK IC50 (nM) |
|---|---|---|---|---|---|
| 28 | 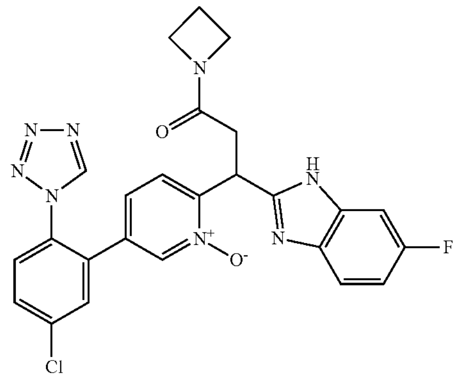 [SMILES: O=C(CC(c1nc2ccc(F)cc2[nH]1)c1ccc(-c2cc(Cl)ccc2-n2cnnn2)c[n+]1[O-])N1CCC1] | slow eluting isomer, chiral IA column, 70% 2:1 MeOH:MeCN/CO2 | 519 | 93.68 | 1814.00 |

Factor XIa Assay

The effectiveness of a compound of the present invention as an inhibitor of Coagulation Factor XIa can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 150 mM NaCl, 5 mM $CaCl_2$, and 0.1% PEG 8000 (polyethylene glycol; JT Baker or Fisher Scientific). Determinations were made using purified human Factor XIa at a final concentration of 40 pM (Sekisui Diagnostics) and the synthetic substrate, Z-Gly-Pro-Arg-AFC, TFA salt (Sigma #C0980) at a concentration of 100 µM.

Activity assays were performed by diluting a stock solution of substrate at least tenfold to a final concentration ≤0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m/[S]$, [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in the following equation.

$$V_o/V_i = 1 + [I]/K_i$$

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

Kallikrein Assay

The effectiveness of a compound of the present invention as an inhibitor of Kallikrein can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_i$.

Kallikrein determinations were made in 50 mM HEPES buffer at pH 7.4 containing 150 mM NaCl, 5 mM $CaCl_2$, and 0.1% PEG 8000 (polyethylene glycol; Fisher Scientific). Determinations were made using purified Human plasma kallikrein at a final concentration of 0.5 nM (Enzyme Research Laboratories) and the synthetic substrate, Acetyl-K—P—R-AFC (Sigma # C6608) at a concentration of 100 mM.

Activity assays were performed by diluting a stock solution of substrate at least tenfold to a final concentration ≤0.2 $K_m$ into a solution containing enzyme or enzyme equilibrated with inhibitor. Times required to achieve equilibration between enzyme and inhibitor were determined in control experiments. The reactions were performed under linear progress curve conditions and fluorescence increase measured at 405 Ex/510 Em nm. Values were converted to percent inhibition of the control reaction (after subtracting 100% Inhibition value). $IC_{50}$ was determined by inflection point from a four parameter logistic curve fit. Ki was calculated using the Cheng Prusoff equation, $Ki = IC_{50}/(1+ ([S]/Km))$.

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

What is claimed is:

1. A compound of the formula:

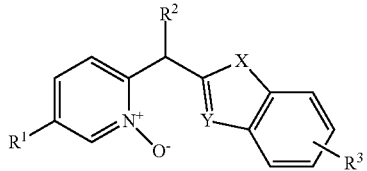

wherein X is NH;
Y is N;
$R^1$ is aryl or $C_{3-6}$ cycloalkyl, wherein said aryl and cycloalkyl groups are optionally substituted with one to three substituents independently selected from the group consisting of halo, nitro, cyano, oxo, $R^4$, $OR^4$, (C=O)$R^4$, (C=O)$OR^4$, (C=O)$NR^4R^5$, $NR^4R^5$, NH(C=O)$R^4$, NH(C=O)$OR^4$, C(NH)$NR^4R^5$, $C_{3-6}$ cycloalkyl and tetrazolyl which is optionally substituted with $R^4$;

$R^2$ is hydrogen or CH($R^{2a}$)($R^{2b}$);

$R^{2a}$ is hydrogen, $C_{1-6}$ alkyl, aryl or $C_{3-6}$ cycloalkyl, wherein said alkyl group is optionally substituted with one to three substituents independently selected from the group consisting of halo, hydroxy and cyano, and wherein said aryl, and cycloalkyl groups are optionally substituted with one to three substituents independently selected from the group consisting of halo, nitro, cyano, oxo, $R^4$ and $OR^4$;

$R^{2b}$ is hydrogen or $C_{1-6}$ alkyl, which is optionally substituted with one to three substituents independently selected from the group consisting of halo, hydroxy and cyano;

$R^3$ is halo, cyano, (C=O)$OR^4$ or $R^6$;

$R^4$ is hydrogen or $C_{1-6}$ alkyl, which is optionally substituted with one to three groups independently selected from the group consisting of halo and hydroxy;

$R^5$ is hydrogen or $C_{1-6}$ alkyl, which is optionally substituted with one to three groups independently selected from the group consisting of halo and hydroxy;

$R^6$ is aryl or $C_{3-10}$ cycloalkyl, wherein said aryl and cycloalkyl groups are optionally substituted with one to three substituents independently selected from the group consisting of halo, nitro, cyano, oxo, $R^4$, $OR^4$, (C=O)$R^4$, (C=O)$OR^4$, (C=O)$NR^4R^5$, $NR^4R^5$, NH(C=O)$R^4$, NH(C=O)$OR^4$, $SO_2R^4$, $SO_2NR^4R^5$, $NR^4SO_2R^5$ and $PO_3R^4$; or a pharmaceutically acceptable salt thereof.

2. The compound of claim 1 of the formula:

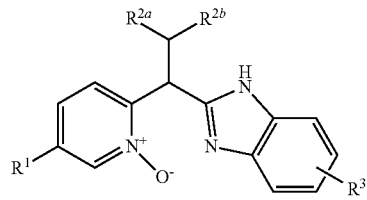

wherein $R^1$ is aryl or $C_{3-6}$ cycloalkyl, wherein said aryl and cycloalkyl groups are optionally substituted with one to three substituents independently selected from the group consisting of halo, nitro, cyano, oxo, $R^4$, $OR^4$, (C=O)$R^4$, (C=O)$OR^4$, (C=O)$OR^4$, $NR^4R^5$, NH(C=O)$R^4$, NH(C=O)$OR^4$, C(NH)$NR^4R^5$, $C_{3-6}$ cycloalkyl and tetrazolyl which is optionally substituted with $R^4$;

$R^{2a}$ is hydrogen, $C_{1-6}$ alkyl, aryl or $C_{3-6}$ cycloalkyl, wherein said alkyl group is optionally substituted with one to three substituents independently selected from the group consisting of halo, hydroxy and cyano, and wherein said aryl and cycloalkyl groups are optionally substituted with one to three substituents independently selected from the group consisting of halo, nitro, cyano, oxo, $R^4$ and $OR^4$;

$R^{2b}$ is hydrogen or $C_{1-6}$ alkyl, which is optionally substituted with one to three substituents independently selected from the group consisting of halo, hydroxy and cyano;

$R^3$ is halo, cyano, (C=O)$OR^4$ or $R^6$;

$R^4$ is hydrogen or $C_{1-6}$ alkyl, which is optionally substituted with one to three groups independently selected from the group consisting of halo and hydroxy;

$R^5$ is hydrogen or $C_{1-6}$ alkyl, which is optionally substituted with one to three groups independently selected from the group consisting of halo and hydroxy;

$R^6$ is aryl or $C_{3-10}$ cycloalkyl, wherein said aryl and cycloalkyl groups are optionally substituted with one to three substituents independently selected from the group consisting of halo, nitro, cyano, oxo, $R^4$, $OR^4$, (C=O)$R^4$, (C=O)$OR^4$, (C=O)$NR^4R^5$, $NR^4R^5$, NH(C=O)$R^4$, NH(C=O)$OR^4$, $SO_2R^4$, $SO_2NR^4R^5$, $NR^4SO_2R^5$ and $PO_3R^4$;

or a pharmaceutically acceptable salt thereof.

3. The compound of claim 1 wherein $R^1$ is aryl, which optionally is substituted with one to three substituents independently selected from the group consisting of halo, cyano, $OR^4$, $R^4$, $C_{3-6}$ cycloalkyl and tetrazolyl which is optionally substituted with $R^4$; or a pharmaceutically acceptable salt thereof.

4. The compound of claim 1 wherein $R^1$ is phenyl, which optionally is substituted with one to three substituents independently selected from the group consisting of halo, $C_{3-6}$ cycloalkyl and tetrazolyl; or a pharmaceutically acceptable salt thereof.

5. The compound of claim 1 wherein $R^{2a}$ is aryl, which optionally is substituted with one to three halo; or a pharmaceutically acceptable salt thereof.

6. The compound of claim 1 wherein $R^{2b}$ is hydrogen; or a pharmaceutically acceptable salt thereof.

7. The compound of claim 1 wherein $R^{2a}$ is cyclopropyl; or a pharmaceutically acceptable salt thereof.

8. The compound of claim 1 wherein $R^3$ is halo, cyano or (C=O)$OR^4$; or a pharmaceutically acceptable salt thereof.

9. The compound of claim 1 wherein R³ is halo; or a pharmaceutically acceptable salt thereof.
10. The compound of claim 1 wherein R³ is (C=O)OR⁴; or a pharmaceutically acceptable salt thereof.
11. The compound selected from:
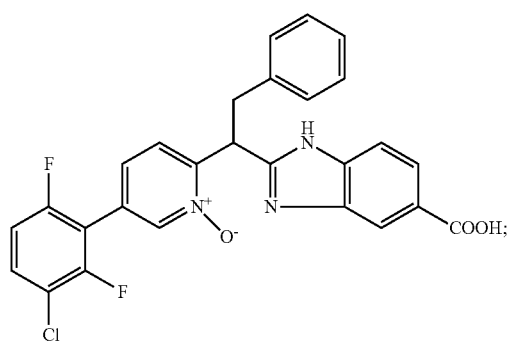
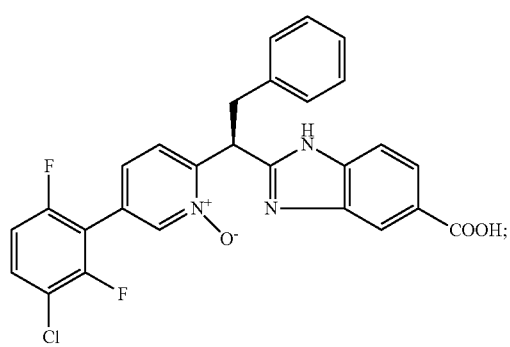
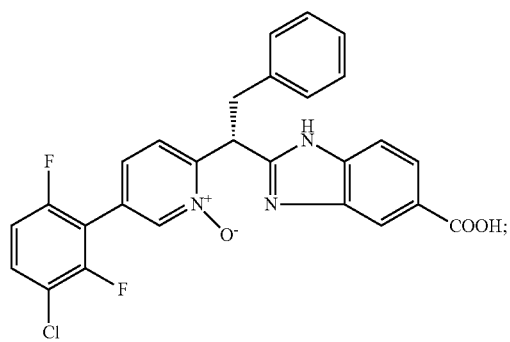
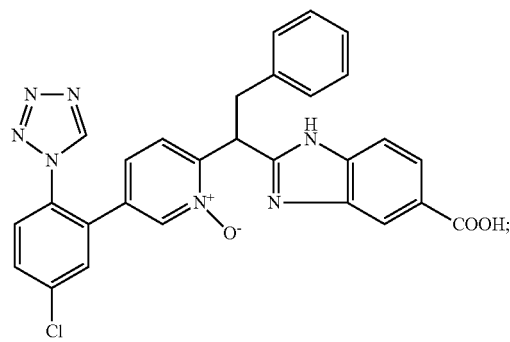
-continued
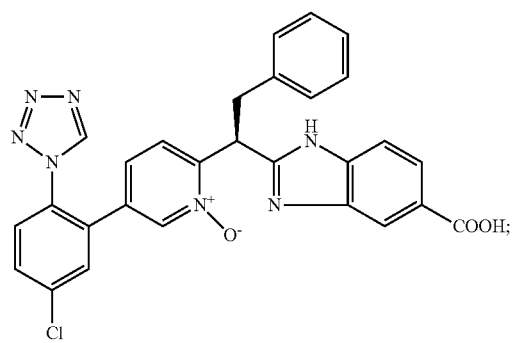
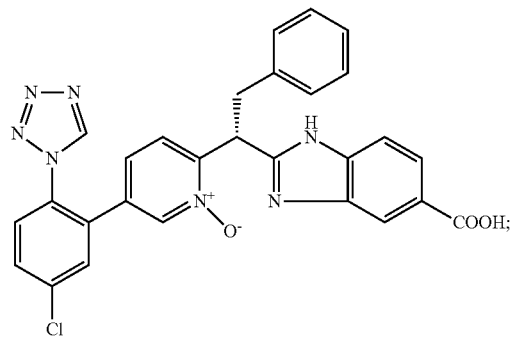
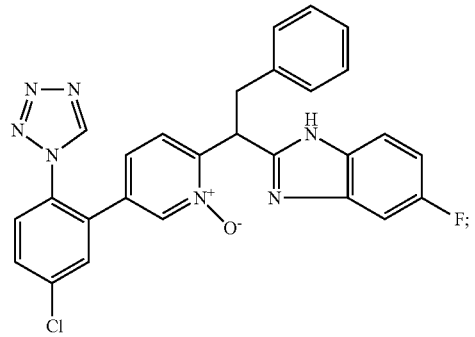
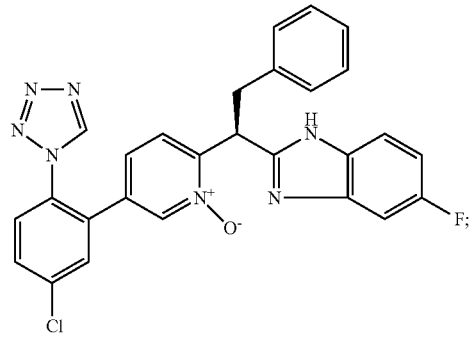
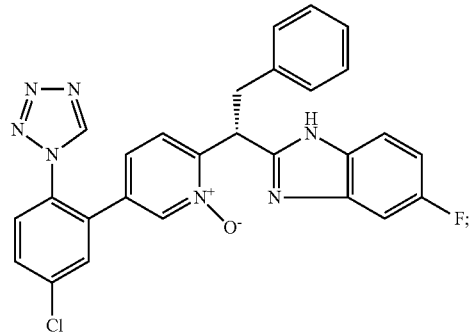

-continued
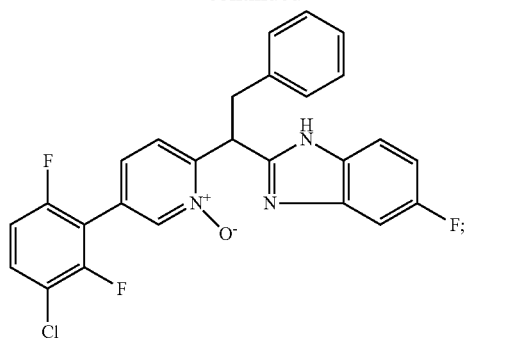
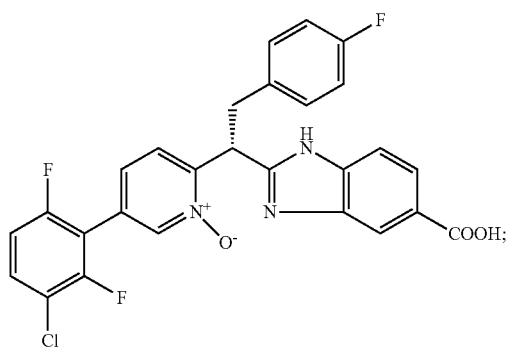
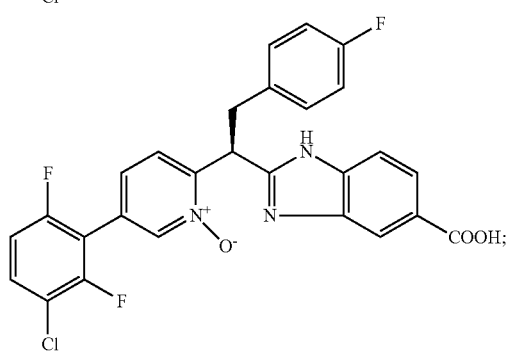
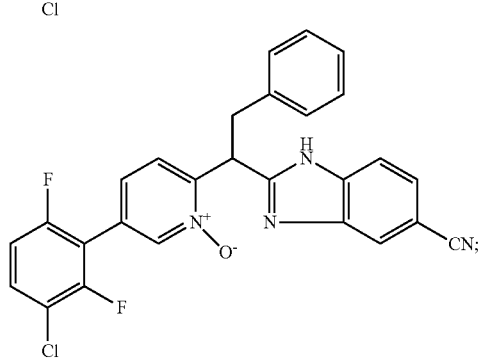
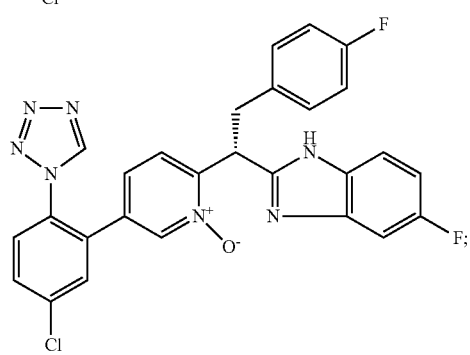
-continued
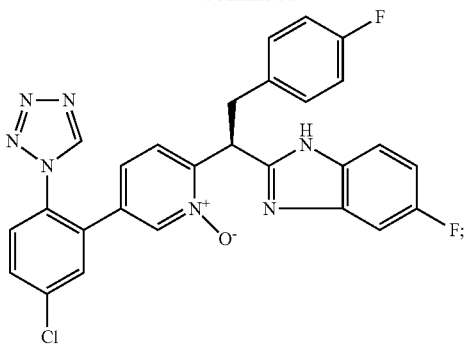
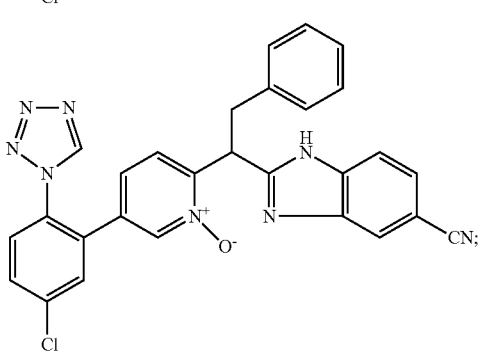
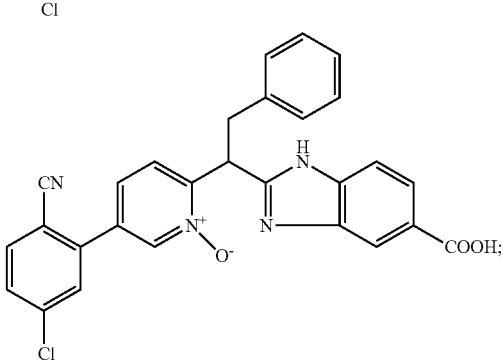
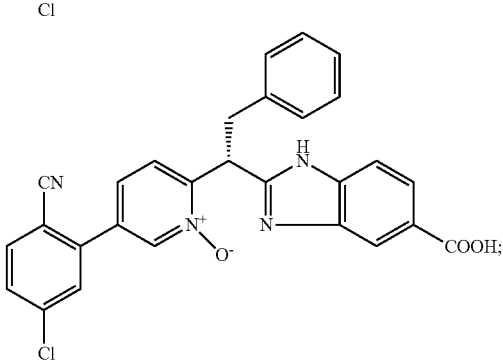
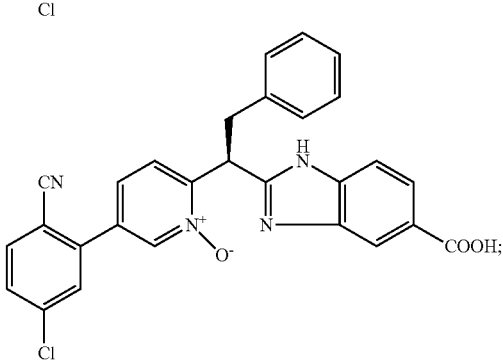

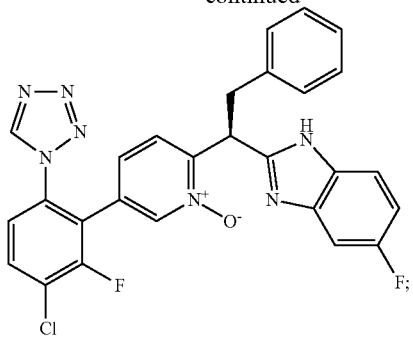
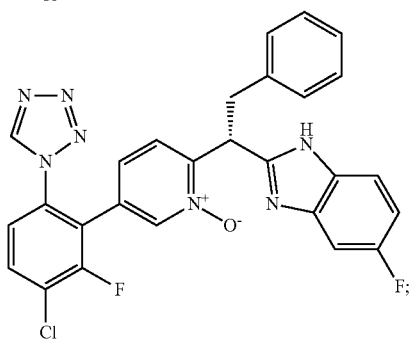
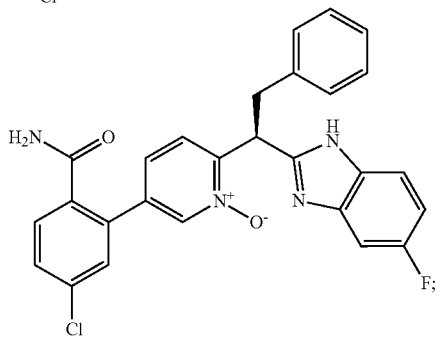
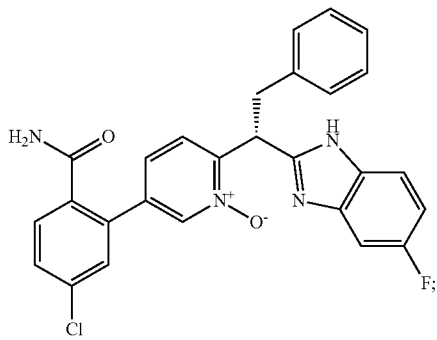
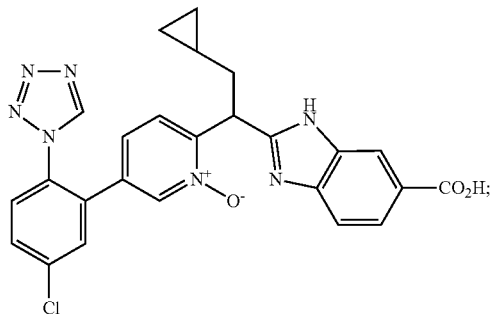
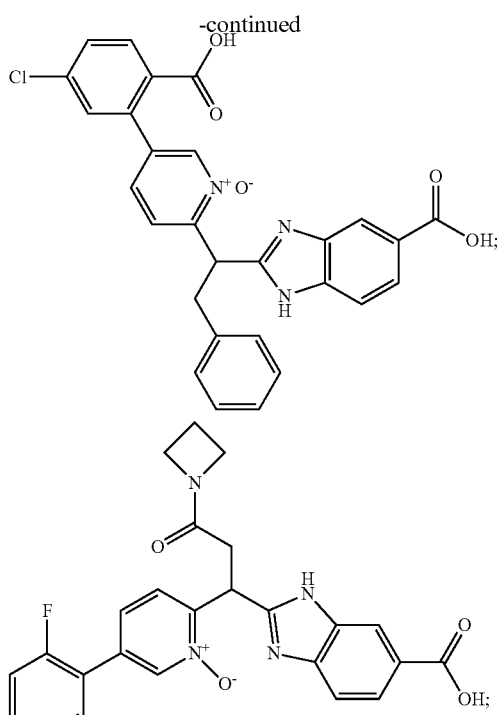
or a pharmaceutically acceptable salt thereof.
12. A pharmaceutical composition comprising a compound of claim 1 or a pharmaceutically acceptable salt thereof and a pharmaceutically acceptable carrier.
* * * * *